US008467880B2

(12) United States Patent
Glukhovsky et al.

(10) Patent No.: US 8,467,880 B2
(45) Date of Patent: Jun. 18, 2013

(54) SYSTEM FOR TRANSMITTING ELECTRICAL CURRENT TO A BODILY TISSUE

(75) Inventors: Arkady Glukhovsky, Santa Clarita, CA (US); Kevin Wilkin, Valencia, CA (US); John Gord, Venice, CA (US); Einan Regev, Kefar Vradim (IL)

(73) Assignee: Bioness Inc., Valencia, CA (US)

( * ) Notice: Subject to any disclaimer, the term of this patent is extended or adjusted under 35 U.S.C. 154(b) by 1185 days.

(21) Appl. No.: 12/197,849

(22) Filed: Aug. 25, 2008

(65) Prior Publication Data

US 2009/0054952 A1    Feb. 26, 2009

Related U.S. Application Data

(60) Provisional application No. 60/957,592, filed on Aug. 23, 2007.

(51) Int. Cl.
*A61N 1/18*    (2006.01)
(52) U.S. Cl.
USPC .............................. 607/48; 607/46; 607/115
(58) Field of Classification Search
USPC   607/46–48, 115–116, 144, 149–152; 604/20, 604/501
See application file for complete search history.

(56) References Cited

U.S. PATENT DOCUMENTS 3,835,864 A    9/1974  Rasor et al.
4,032,860 A *  6/1977  LeVeen ............................ 331/63

(Continued)

FOREIGN PATENT DOCUMENTS

DE    4331945 A1    3/1995
JP    62-270173 A   11/1987

(Continued)

OTHER PUBLICATIONS

Lee, C. "Scientists create paper-thin, flexible, biodegradable battery", [online] Retrieved from the Internet on Jun. 20, 2008. Retrieved from URL: <<http://arstechnica.com/news.ars/post/20070813-scientists-create-paper-thin-flexible-biodegradable-battery.html>>.

(Continued)

*Primary Examiner* — Rex R Holmes
(74) *Attorney, Agent, or Firm* — Cooley LLP

(57) ABSTRACT

In some embodiments, an apparatus includes a substrate, a power source, a connector, electrical circuitry, and an electrode assembly. The substrate has a first surface and a second surface different than the first surface. The power source has a positive terminal and a negative terminal Each of the positive terminal and the negative terminal are coupled to the substrate. The power source is configured to provide power to an external stimulator coupled to the apparatus. The connector is disposed proximate to the first surface of the substrate and is electrically coupled to at least one of the positive terminal and the negative terminal of the power source. The connector is configured to electrically couple the external stimulator to the power source. The electrical circuitry is coupled to the substrate. The electrical circuitry is configured to electrically couple the connector to at least one of the positive terminal and the negative terminal of the power source. At least one of the connector or the electrical circuitry is configured to prevent a short circuit of the electrical circuit. The electrode assembly is coupled to the second surface of the substrate. At least one electrode of the electrode assembly is configured to contact bodily tissue and to facilitate transmission of an electrical current through the bodily tissue.

19 Claims, 15 Drawing Sheets

U.S. PATENT DOCUMENTS

| | | | |
|---|---|---|---|
| 4,088,141 A | 5/1978 | Niemi | |
| 4,102,344 A | 7/1978 | Conway et al. | |
| 4,323,999 A | 4/1982 | Yoshizawa et al. | |
| 4,419,995 A | 12/1983 | Hochmair et al. | |
| 4,699,143 A | 10/1987 | Dufresne et al. | |
| 4,702,732 A | 10/1987 | Powers et al. | |
| 4,832,032 A | 5/1989 | Schneider | |
| 5,080,099 A | 1/1992 | Way et al. | |
| 5,097,833 A | 3/1992 | Campos | |
| 5,169,384 A | 12/1992 | Bosniak et al. | |
| 5,246,418 A | 9/1993 | Haynes et al. | |
| 5,325,870 A * | 7/1994 | Kroll et al. | 607/122 |
| 5,330,516 A | 7/1994 | Nathan | |
| 5,356,428 A | 10/1994 | Way | |
| 5,387,189 A | 2/1995 | Gory et al. | |
| 5,397,338 A | 3/1995 | Grey et al. | |
| 5,465,715 A | 11/1995 | Lyons | |
| 5,487,759 A | 1/1996 | Bastyr et al. | |
| 5,514,165 A | 5/1996 | Malaugh et al. | |
| 5,531,782 A * | 7/1996 | Kroll et al. | 607/122 |
| 5,545,191 A | 8/1996 | Mann et al. | |
| 5,562,707 A | 10/1996 | Prochazka et al. | |
| 5,578,065 A | 11/1996 | Hattori et al. | |
| 5,613,943 A | 3/1997 | Palumbo | |
| 5,674,261 A | 10/1997 | Smith | |
| 5,766,231 A | 6/1998 | Erickson et al. | |
| 5,807,397 A | 9/1998 | Barreras | |
| 5,814,090 A | 9/1998 | Latterell et al. | |
| 5,879,322 A | 3/1999 | Lattin et al. | |
| 5,916,244 A | 6/1999 | Walters | |
| 5,948,006 A | 9/1999 | Mann | |
| 6,002,965 A | 12/1999 | Katz et al. | |
| 6,073,050 A * | 6/2000 | Griffith | 607/57 |
| 6,214,032 B1 | 4/2001 | Loeb et al. | |
| 6,282,448 B1 | 8/2001 | Katz et al. | |
| 6,366,814 B1 | 4/2002 | Boveja et al. | |
| 6,377,848 B1 | 4/2002 | Garde et al. | |
| 6,438,428 B1 | 8/2002 | Axelgaard et al. | |
| 6,445,955 B1 * | 9/2002 | Michelson et al. | 607/46 |
| 6,564,102 B1 | 5/2003 | Boveja | |
| 6,607,500 B2 | 8/2003 | Da Silva et al. | |
| 6,629,968 B1 | 10/2003 | Jain et al. | |
| 6,635,045 B2 | 10/2003 | Keusch et al. | |
| 6,668,191 B1 | 12/2003 | Boveja | |
| 6,735,474 B1 | 5/2004 | Loeb et al. | |
| 6,735,475 B1 | 5/2004 | Whitehurst et al. | |
| 6,754,472 B1 | 6/2004 | Williams et al. | |
| 6,788,979 B1 | 9/2004 | Axelgaard et al. | |
| 6,840,919 B1 | 1/2005 | Håkansson | |
| 6,879,859 B1 | 4/2005 | Boveja | |
| 6,892,098 B2 | 5/2005 | Ayal et al. | |
| 6,896,675 B2 | 5/2005 | Leung et al. | |
| 6,928,320 B2 | 8/2005 | King | |
| 6,941,171 B2 | 9/2005 | Mann et al. | |
| 6,961,623 B2 | 11/2005 | Prochazka | |
| 7,047,071 B2 | 5/2006 | Wagner et al. | |
| 7,096,064 B2 | 8/2006 | Deno et al. | |
| 7,146,210 B2 | 12/2006 | Palti | |
| 7,242,982 B2 | 7/2007 | Singhal et al. | |
| 7,324,853 B2 | 1/2008 | Ayal et al. | |
| 7,389,145 B2 | 6/2008 | Kilgore et al. | |
| 7,502,652 B2 | 3/2009 | Gaunt et al. | |
| 7,536,226 B2 | 5/2009 | Williams et al. | |
| 2002/0019652 A1 | 2/2002 | Da Silva | |
| 2002/0055761 A1 | 5/2002 | Mann et al. | |
| 2002/0058982 A1 | 5/2002 | Axelgaard et al. | |
| 2002/0151951 A1 | 10/2002 | Axelgaard et al. | |
| 2002/0193844 A1 * | 12/2002 | Michelson et al. | 607/48 |
| 2003/0078642 A1 | 4/2003 | Malaney et al. | |
| 2003/0171792 A1 | 9/2003 | Zarinetchi et al. | |
| 2003/0199807 A1 | 10/2003 | Dent et al. | |
| 2003/0212440 A1 | 11/2003 | Boveja | |
| 2004/0130455 A1 | 7/2004 | Prochazka | |
| 2004/0176804 A1 | 9/2004 | Palti | |
| 2004/0199222 A1 | 10/2004 | Sun et al. | |
| 2005/0070970 A1 | 3/2005 | Knudson et al. | |
| 2005/0136385 A1 | 6/2005 | Mann et al. | |
| 2005/0165461 A1 * | 7/2005 | Takeda et al. | 607/61 |
| 2005/0277841 A1 * | 12/2005 | Shennib | 600/511 |
| 2006/0064140 A1 | 3/2006 | Whitehurst et al. | |
| 2006/0206165 A1 | 9/2006 | Jaax et al. | |
| 2006/0271118 A1 | 11/2006 | Libbus et al. | |
| 2007/0060975 A1 | 3/2007 | Mannheimer et al. | |
| 2007/0088419 A1 | 4/2007 | Fiorina et al. | |
| 2008/0004676 A1 | 1/2008 | Osypka et al. | |
| 2008/0046053 A1 | 2/2008 | Wagner et al. | |
| 2008/0243216 A1 | 10/2008 | Zilberman et al. | |
| 2008/0288026 A1 * | 11/2008 | Cross et al. | 607/60 |
| 2009/0177131 A1 | 7/2009 | Dar et al. | |
| 2009/0222053 A1 | 9/2009 | Gaunt | |
| 2009/0326602 A1 | 12/2009 | Glukhovsky et al. | |
| 2010/0016929 A1 | 1/2010 | Prochazka | |
| 2010/0076533 A1 | 3/2010 | Dar et al. | |
| 2010/0198298 A1 | 8/2010 | Glukhovsky et al. | |

FOREIGN PATENT DOCUMENTS

| | | |
|---|---|---|
| JP | 63-317164 A | 12/1988 |
| JP | 2-234774 A | 9/1990 |
| JP | 8-66842 A | 3/1996 |
| JP | 9-66110 A | 3/1997 |
| JP | 2002-517293 A | 6/2002 |
| JP | 2003-501207 | 1/2003 |
| JP | 2003-512139 A | 4/2003 |
| JP | 2004-501727 A | 1/2004 |
| JP | 2005-237941 | 9/2005 |
| WO | WO 95/10323 | 4/1995 |
| WO | WO 01/03768 A1 | 1/2001 |
| WO | WO 02/02182 A2 | 1/2002 |
| WO | WO 2005/011541 A1 | 2/2005 |
| WO | WO 2005/070494 A1 | 8/2005 |
| WO | WO 2006/101917 A2 | 9/2006 |
| WO | WO 2006/113654 A1 | 10/2006 |
| WO | WO 2006/113801 A2 | 10/2006 |
| WO | WO 2007/002741 A1 | 1/2007 |
| WO | WO 2008/140242 A1 | 11/2008 |
| WO | WO 2009/058258 A1 | 5/2009 |

OTHER PUBLICATIONS

Solo Instructions for Use, Shire, Moat Farm, Case Lane, Five Ways, Hatton, Warks, CV35 7JD—Issued Mar. 9, 2000; 6 pages.

Gan, L. et al. "The Stimulus Router: A Novel Means of Directing Current From Surface Electrodes to Nerves." 10th Annual Conference of the International FES Society, Jul. 2005, Montreal, Canada, pp. 21-23.

Prochazka, A. Neural Prosthesis Program Meeting, NIH Meeting, Nov. 2004; 5 pages.

International Search Report and Written Opinion for PCT/US08/74252, mailed on Nov. 3, 2008; 10 pages.

Supplementary Search Report for European Patent Application No. 08827776.9, mailed Mar. 10, 2011.

Office Action for U.S. Appl. No. 12/400,202, mailed Mar. 5, 2012.

Office Action for U.S. Appl. No. 12/400,202, mailed Aug. 8, 2012.

Notice of Reasons for Rejection for Japanese Application No. 2010-522104, mailed Feb. 12, 2013.

* cited by examiner

SYSTEM FOR TRANSMITTING ELECTRICAL CURRENT TO A BODILY TISSUE

CROSS-REFERENCE TO RELATED APPLICATIONS

This application claims priority to U.S. Provisional Application Ser. No. 60/957,592, entitled "System for Transmitting Electrical Current to a Bodily Tissue," filed Aug. 23, 2007, which is incorporated herein by reference in its entirety.

BACKGROUND

The invention relates generally to medical devices, and specifically to a device for transmitting an electrical stimulation to a bodily tissue of a patient.

Known electrical stimulation systems are used in various medical procedures. For example, some known electrical stimulation systems are used to stimulate a response from a bodily organ or tissue of a patient, such as, for example, the heart, a muscle group or the like. Some known electrical stimulation systems are used to treat acute and/or chronic pain. One known electrical stimulation system, for example, is a transcutaneous electrical nerve stimulation (TENS) unit that provides an electrical stimulation to an electrode attached to the skin of the patient. The TENS unit includes a battery that must be sufficiently large to provide enough energy for a desired treatment period, often a period of several months, of electrical stimulation before replacement. Such a battery, however, may be obtrusive and/or burdensome for a patient to wear, for example, when the patient is in a long-term treatment program. The TENS unit is connected to the skin electrodes by wires extending from the unit to the electrodes. Exposure of such wires to moisture or fluid, for example as occurs during bathing, swimming, and/or perspiration, may result in unintended current loss or transfer, or shorting of the battery. The presence of such wires can also be cumbersome and/or aesthetically unappealing for the patient. Furthermore, the electrode can lose its electrical and/or mechanical properties within several days, so regular replacement of the electrode is required.

Some known systems are configured for use with a shorter-life battery; however, the system must be designed with a housing that can be opened to remove a used battery and to insert a new battery. Such a design can result in a bulky device that must be worn by the patient.

Some known systems necessitate several connections between an electrode patch and a stimulator. For example, known systems can include three or four connections between the patch and the stimulator. Each additional connection increases the risk that the battery and/or the electrical circuit can be shorted, for example due to the connectors being exposed to moisture, as described above.

What is needed is a compact medical device having a smaller battery configured to provide power for a greater duration or a duration similar to the length of time during which an electrode retains its electrical and/or mechanical properties on a body of a patient. A need also exists for a compact medical device that is configured to reduce the risk of a short circuit and/or leakage of an electrical current, such as by having a reduced number of mechanical connections with an external stimulator.

SUMMARY OF THE INVENTION

In some embodiments, an apparatus includes a substrate, a power source, a connector, electrical circuitry, and an electrode assembly. The substrate has a first surface and a second surface different than the first surface. The power source has a positive terminal and a negative terminal. Each of the positive terminal and the negative terminal are coupled to the substrate. The power source is configured to provide power to an external stimulator coupled to the apparatus. The connector is disposed proximate to the first surface of the substrate and is electrically coupled to at least one of the positive terminal and the negative terminal of the power source. The connector is configured to electrically couple the external stimulator to the power source. The electrical circuitry is coupled to the substrate. The electrical circuitry is configured to electrically couple the connector to at least one of the positive terminal and the negative terminal of the power source. At least one of the connector or the electrical circuitry is configured to prevent a short circuit of the electrical circuit. The electrode assembly is coupled to the second surface of the substrate. At least one electrode of the electrode assembly is configured to contact bodily tissue and to facilitate transmission of an electrical current through the bodily tissue.

DETAILED DESCRIPTION

Figure 1:
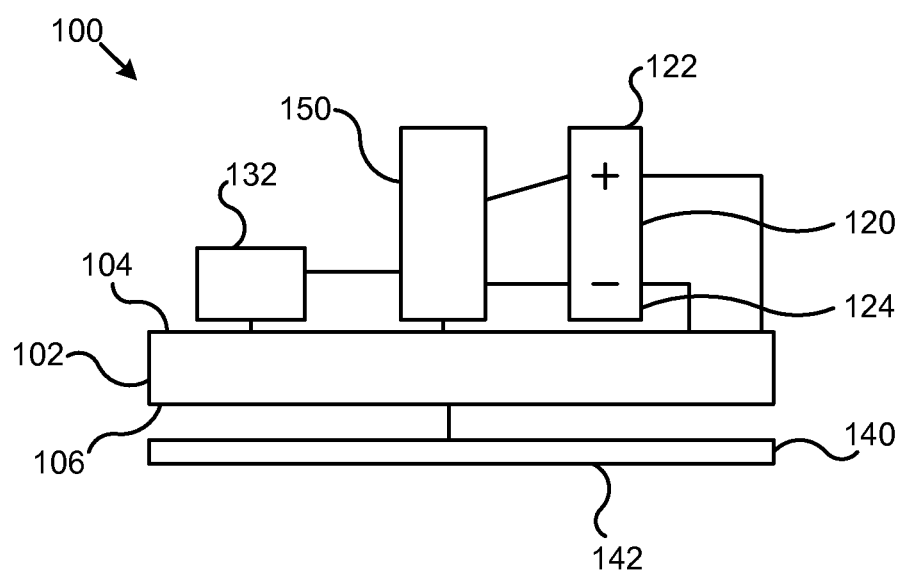
FIG. 1 is a schematic illustration of an apparatus according to an embodiment.

Apparatus and methods for transmitting an electrical stimulation from an external stimulator to a bodily tissue of a patient are described herein. In some embodiments, an apparatus is configured to be disposed on bodily tissue (e.g., skin) of a patient. The apparatus is configured to receive an electrical input from an external stimulator via a connector and to transmit the electrical input as an electrical current to an electrode disposed on or proximate to the bodily tissue. In this manner, the apparatus transmits the electrical stimulation to the bodily tissue.

As used herein, bodily tissue can include any tissue of a patient suitable for receiving an electrical stimulation. Bodily tissue can include, for example, nervous tissue, such as a nerve, the spinal cord, or another component of the peripheral or central nervous system. In another example, bodily tissue can include muscle tissue, such as, for example, skeletal muscle, smooth muscle, or cardiac muscle. Specifically, bodily tissue can include a group of tissues forming an organ, such as, for example, the skin, lungs, cochlea, heart, bladder, or kidney. In still another example, bodily tissue can include connective tissue, such as, for example, bone or bone-like tissue.

The apparatus is configured to treat a variety of medical conditions, including acute and/or chronic pain, and/or to activate a motor point. For example, the apparatus can be configured to transmit an electrical current that at least partially activates conduction and/or propagation of action potentials (nerve impulses) along the axons of a target nerve associated with a target bodily tissue. In another example, the apparatus can be configured to transmit to the bodily tissue an electrical current that at least partially blocks the conduction and/or propagation of action potentials along the axons of the target nerve associated with the target bodily tissue.

The apparatus can be configured for transcutaneous and/or percutaneous stimulation of the target bodily tissue. In a treatment or procedure for transcutaneous stimulation, for example, the apparatus is configured to transmit an electrical stimulation through bodily tissue from a first electrode positioned on a first location of the patient's skin to a second electrode positioned on a second location on the patient's skin different from the first location. The pathway of the electrical current through the bodily tissue of the patient is a transcutaneous stimulation pathway. In a treatment or procedure for percutaneous stimulation, for example, the apparatus is configured to transmit an electrical stimulation to bodily tissue via an electrical lead. The electrical lead helps direct the electrical current to the target bodily tissue. In some procedures, the electrical lead can be completely implanted within the bodily tissue. In other procedures, the electrical lead is partially implanted within the bodily tissue such that a portion of the lead extends through the skin.

As used in this specification, the singular forms "a," "an" and "the" include plural referents unless the context clearly dictates otherwise. Thus, for example, the term "a material" is intended to mean one or more materials, or a combination thereof.

FIG. 1 is a schematic illustration of an apparatus 100 according to an embodiment. The apparatus 100 is configured to transmit an electrical current from a stimulator (not shown) through a bodily tissue of a patient. In this manner, the apparatus 100 is configured to stimulate a target bodily tissue. The apparatus 100 can be, for example, an electrode-battery assembly.

The apparatus 100 is configured to be disposed on or proximate to a patient's body, for example, on the skin of the patient. The apparatus 100 can be coupled to the skin of the patient with an adhesive, a bandage, or the like, or any combination of the foregoing.

The apparatus 100 includes a substrate 102, a power source 120, a connector 132, electrical circuitry 150, and an electrode assembly 140. The substrate 102 has a first surface 104 and a second surface 106 different than the first surface 104. The substrate 102 is configured to be disposed on or proximate to the body of the patient. When the apparatus 100 is disposed on the patient's body, the second surface 106 of the apparatus faces the patient's tissue, e.g., the skin.

The power source 120 is configured to provide power to an external stimulator (not shown) coupled to the apparatus 100. The power source 120 can be any suitable energy supplying source. For example, in some embodiments, the power source 120 is a battery. In some embodiments, the power source 120 is an ultracapacitor or a supercapacitor. The power source 120 is coupled to the substrate 102. In the schematic illustration, the power source 120 has a positive terminal 122 and a negative terminal 124. Each of the positive terminal 122 and the negative terminal 124 are coupled to the substrate 102.

The connector 132 is configured to electrically couple the external stimulator to the power source 120. The connector 132 can be any suitable mechanism for electrically coupling the external stimulator and the power source 120. For example, in some embodiments, the connector 132 is configured to provide both a mechanical and an electrical connection between the apparatus 100 and the external stimulator. Said another way, when the external stimulator is mechanically coupled to the apparatus 100 via the connector 132, the external stimulator is also placed in electrical communication with the power source 120. The connector 132 can be any suitable connector, including but not limited to, a snap-fit connector. In some embodiments, the connector 132 is a metal electrode. In some embodiments, the connector 132 is configured to provide a wireless electrical connection between the external stimulator and the power source 120. In some embodiments, for example, the connector is an antenna configured to transmit a signal to and/or receive a signal from the external stimulator. In some embodiments, the connector is a conductive ink, a wire, or the like.

The connector 132 is disposed proximate to the first surface 104 of the substrate 102. In some embodiments, for example, the connector is embedded in the first surface 104 of the substrate 102. In some embodiments, the connector 132 is disposed on top of the first surface 104 of the substrate 102. For example, the connector 132 can be a conductive ink printed onto the first surface 104 substrate. In still other embodiments, a portion of the connector 132 is embedded in the substrate and another portion of the connector extends from the first surface 104. As illustrated in FIG. 1, the connector 132 is electrically coupled to at least one of the positive terminal 122 and the negative terminal 124 of the power source 120.

The electrical circuitry 150 is coupled to the substrate 102. The electrical circuitry 150 is configured to electrically couple the connector 132 to the at least one of the positive terminal 122 and the negative terminal 124 of the power source 120. In some embodiments, for example, the electrical circuitry 150 includes a wire configured to electrically connect the connector to the power source 120. In some embodiments, a portion of the electrical circuitry 150 is a pathway of conductive ink printed onto the substrate 102.

At least one of the connector 132 or the electrical circuitry 150 is configured to prevent a short circuit of the electrical circuit. The electrical circuitry 150 can include a variety of suitable mechanisms configured to prevent shorting the electrical circuit (including shorting of the power source 120). For example, in some embodiments, the electrical circuitry 150 includes a fuse configured to open the electrical circuit in the presence of a threshold electrical load. In some embodiments, the electrical circuitry 150 includes a switch biased towards an open position such that the electrical circuit is incomplete until the switch is moved to a closed position. In some embodiments, the electrical circuitry 150 includes a diode configured to prevent flow of an electrical current in an undesired direction. In some embodiments, the connector 132 is configured as a wireless connector. For example, the connector 132 can be an antenna or a coil configured to wirelessly transmit and/or receive an electrical current between the external stimulator and the power source 120. In this manner, the connector 132 can be disposed below a surface of the apparatus 100 or otherwise covered such that the connector 132 is isolated from sources of moisture.

The electrode assembly 140 is coupled to the second surface 106 of the substrate 102. The electrode assembly 140 includes at least one electrode 142. The electrode 142 is configured to contact bodily tissue. For example, in some embodiments, the apparatus 100 includes a gel electrode 142 configured to adhere to the patient's skin. The electrode 142 is configured to facilitate transmission of an electrical current through the bodily tissue.

FIGS. 2-8 illustrate an apparatus 200 according to an embodiment. The apparatus 200 is configured to be disposed on a tissue (e.g., the skin) of a patient. The apparatus 200 includes a substrate 202, a power source 220, a connection assembly 230, electrical circuitry 250, and an electrode assembly 240.

The substrate 202 of the apparatus 200 is a printed circuit board ("PCB"). The PCB 202 has a first surface 204 (see, e.g., FIG. 2) and a second surface 206 (see, e.g., FIG. 4). In use, the second surface 206 of the PCB 202 faces the body of the patient and the first surface 204 faces away from the body of the patient. The PCB 202 is flexible such that the PCB can substantially conform to the contours of the portion of the patient's body on which the apparatus 200 is disposed. For example, the PCB 202 can be configured to be flexible such that the PCB conforms to the curvature of a patient's arm, leg, or back. In this manner, the PCB 202 is configured to facilitate positioning and placement of the apparatus 200 on the patient's body.

Figure 2:
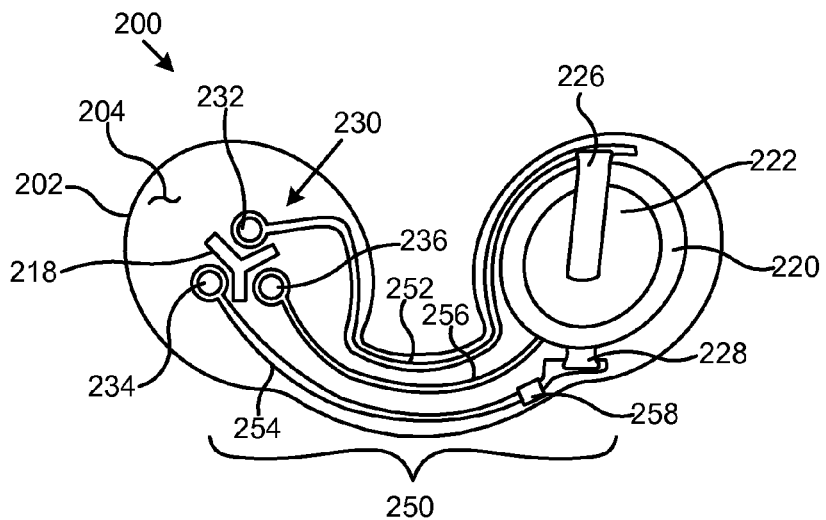
FIG. 2 is a top view of an apparatus according to an embodiment.
Figure 3A:
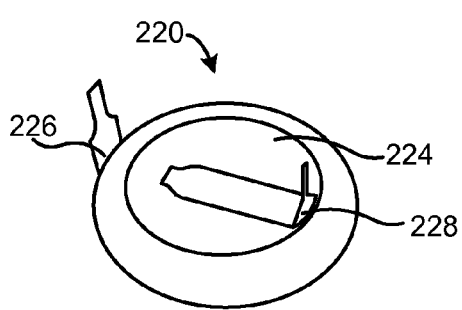
FIGS. 3A-3B are perspective views of a negative terminal and a positive terminal, respectively, of a portion of the apparatus of FIG. 2.
Figure 3B:
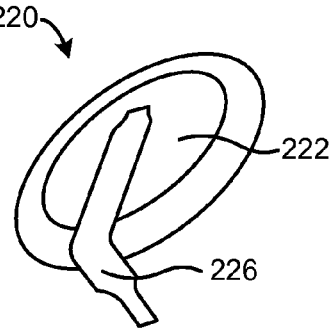

The power source 220 is configured to provide power to an external stimulator S (see, e.g., FIG. 6) coupled to the apparatus 200. The power source 220 is a battery coupled to the PCB 202. Specifically, the battery 220 is coupled to the PCB 202 by electrically conductive tabs 226, 228. As illustrated in FIGS. 2, 3A, and 3B, the battery has a positive terminal 222 and a negative terminal 224. A first electrically conductive tab 226 is coupled to the positive terminal 222. A second electrically conductive tab 228 is coupled to the negative terminal 224. Each of the first and second electrically conductive tabs 226, 228 are coupled to the PCB 202. The electrically conductive tabs 226, 228 can be coupled to the PCB by any suitable coupling mechanism. For example, each electrically conductive tab 226, 228 can be coupled to the PCB 202 by at least one of a solder, a brazer, a weld, an adhesive, a mechanical coupler, or the like, or any combination of the foregoing. Each of the first and second electrically conductive tabs 226, 228 provides an electrical connection between its respective positive terminal 222 or negative terminal 224 of the battery 220 and the electrical circuitry 250, as described in more detail herein.

The connection assembly 230 includes a first connector 232, a second connector 234, and a third connector 236. The connectors 232, 234, 236 are disposed proximate to the first surface 204 of the PCB 202. The first and second connectors 232, 234, in conjunction with the electrical circuitry 250, are configured to electrically couple the battery 220 and the external stimulator S. Specifically, the first connector 232 is electrically coupled to the positive terminal 222 of the battery 220 via the electrical circuitry 250, and the second connector 234 is electrically coupled to the negative terminal 224 of the battery via the electrical circuitry.

The electrical circuitry 250 is at least partially coupled to the PCB 202. In some embodiments, at least a portion of the electrical circuitry 250 is a conductive material printed onto the PCB 202. As illustrated in FIG. 2, the electrical circuitry 250 includes a first electrical pathway 252, a second electrical pathway 254, and a third electrical pathway 256. The first electrical pathway 252 extends from the first connector 232 to the first electrically conductive tab 226, which is coupled to the positive terminal 222 of the battery 220. The first electrical pathway 252 is electrically coupled to the first electrically conductive tab 226, such as by at least one of a solder, a weld, a brazer, a conductive adhesive, a mechanical coupler, or the like, or any combination of the foregoing. Thus, the electrical circuitry 250, via the first electrical pathway 252, electrically couples the first connector 232 to the positive terminal 222 of the battery 220.

The second electrical pathway 254 extends from the second connector 234 to the second electrically conductive tab 228, which is coupled to the negative terminal 224 of the battery 220. The second electrical pathway 254 is electrically coupled to the second electrically conductive tab, such as by at least one of a solder, weld, brazer, or a conductive adhesive, or any combination of the foregoing. Thus, the electrical circuitry 250, via the second electrical pathway 254, electrically couples the second connector 234 to the negative terminal 224 of the battery 220. In this manner, when the external stimulator S is coupled to the apparatus 200 via the first and second connectors 232, 234, a power circuit is completed between the battery 220 and the external stimulator. When the power circuit is completed, the battery 220 can provide power to the external stimulator S, which the external stimulator can use to generate an electrical current for stimulating bodily tissue, as described in more detail herein.

Figure 21:
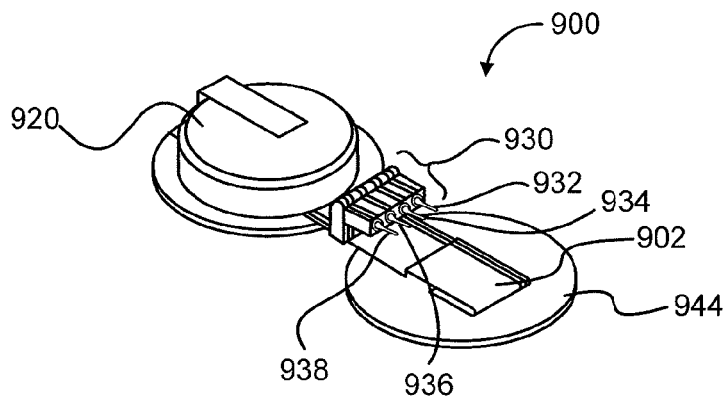
FIG. 21 is a perspective view of a portion of an apparatus according to an embodiment.
Figure 22:
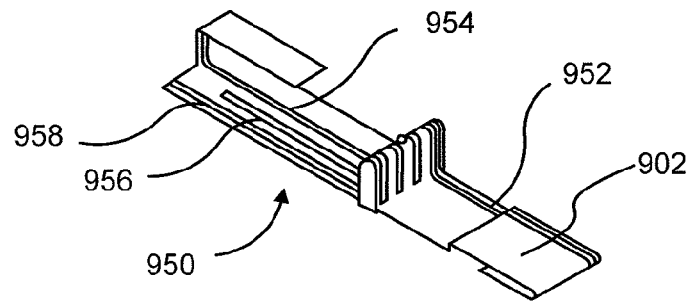
FIG. 22 is a portion of the apparatus of FIG. 21.
Figure 23:
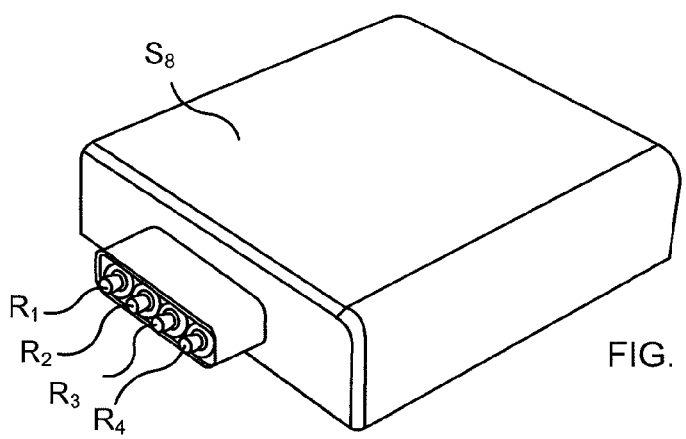
FIG. 23 is an external stimulator configured for use with the apparatus of FIG. 21.

The connection assembly 230 is configured to prevent a short circuit of the electrical circuit. The connection assembly 230 includes a hydrophobic barrier 218 coupled to the substrate 202. As illustrated in FIG. 2, the hydrophobic barrier is a Y-shaped barrier configured to increase impedance of the electrical current between the first connector 232, second connector 234, and/or the third connector 236, for example, when a portion of the substrate is wetted. An experiment testing the impedance of such a barrier is described below with reference to FIGS. 20-22. In use, the apparatus 200 may be wetted or otherwise exposed to a source of moisture, for example water or perspiration, which can create a leakage path for the electrical current between the first connector 232, the second connector 234, and/or the third connector 236 of the connection assembly 230. Such a leakage path for the electrical current can interfere with delivery of the electrical current intended to stimulate the bodily tissue and/or can cause leakage and discharge of the battery 220. The hydrophobic barrier 218 increases the impedance between at least one of the connectors 232, 234, 236 and another of the connectors and/or the wet surface of the substrate 202. The hydrophobic barrier 218 can be constructed of any suitable material, including, but not limited to, plastic, rubber, glue, or another substantially non-conductive material.

The electrical circuitry 250 is also configured to prevent a short circuit of the electrical circuit. Specifically, as illustrated in FIG. 2, the electrical circuitry 250 includes a fuse 258 in the second electrical pathway 254. The fuse 258 is coupled to the PCB 202. For example, the fuse 258 can be at least partially embedded in the PCB 202.

The fuse 258 has a closed configuration and an open configuration. When the fuse 258 is in its closed configuration, the electrical circuitry 250 is configured to allow transfer of an electrical current through the circuitry between the battery 220 and the electrically coupled external stimulator S. In other words, the electrical circuit is closed or complete. When the fuse 258 is in an open configuration, a gap or interruption exists in the second electrical pathway 254. In other words, the electrical circuit is open or incomplete. The transfer of electrical current through the electrical circuitry 250 between the battery 220 and the external stimulator S is inhibited when the circuit is open. As such, the battery 220 is substantially inhibited from providing power to the external stimulator S when the fuse is in its open configuration.

The fuse 258 is configured to be in (or is moved to) its open configuration in the presence of a threshold electrical load. For example, the fuse 258 can be a metal wire or strip configured to melt under an abnormally high electrical load. In another example, the fuse 258 can be configured to break under a threshold electrical load. For example, during use on the body of a patient, the connectors 232, 234, 236 of the connection assembly 230 can be exposed when the external stimulator S is not mechanically coupled to the apparatus 200. The exposed connectors 232, 234, 236 create a risk of shorting the battery 220, for example by exposure to fluid or an electrical charge, which can cause heating and/or explosion of the battery. The fuse 258, however, is configured to open the electrical circuit in the presence of the threshold electrical load to prevent such a short of the battery.

The electrical circuitry 250 also forms a portion of a stimulation circuit. The stimulation circuit includes the third connector 236, a portion of the electrical circuitry 250, such as the third electrical pathway 256, and the electrode assembly 240. The stimulation circuit is complete when the external stimulator is coupled to the third connector 236. The electrical circuitry 250 of the stimulation circuit is configured to receive an electrical current from the external stimulator via the third connector 236. The electrical circuitry 250 is configured to transmit the electrical current to at least one of a first electrode 242 and a second electrode 244. The electrical circuitry 250 is also configured to receive at least a portion of the electrical current from at least one of the first electrode 242 and the second electrode 244. The electrical circuitry 250 transmits the received electrical current to at least one of the external stimulator S or the battery 220.

Figure 4:
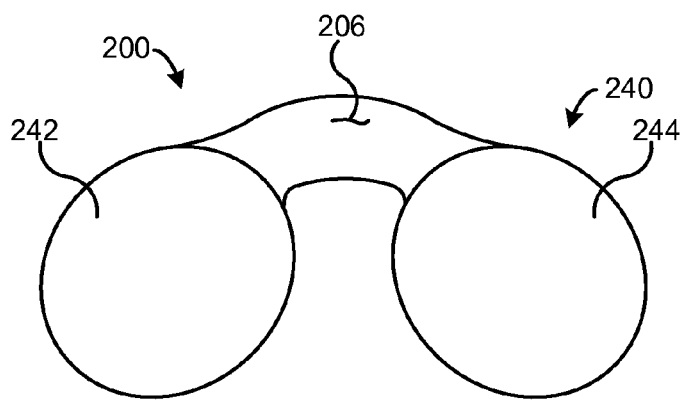
FIG. 4 is a bottom view of the apparatus of FIG. 2.
Figure 7:
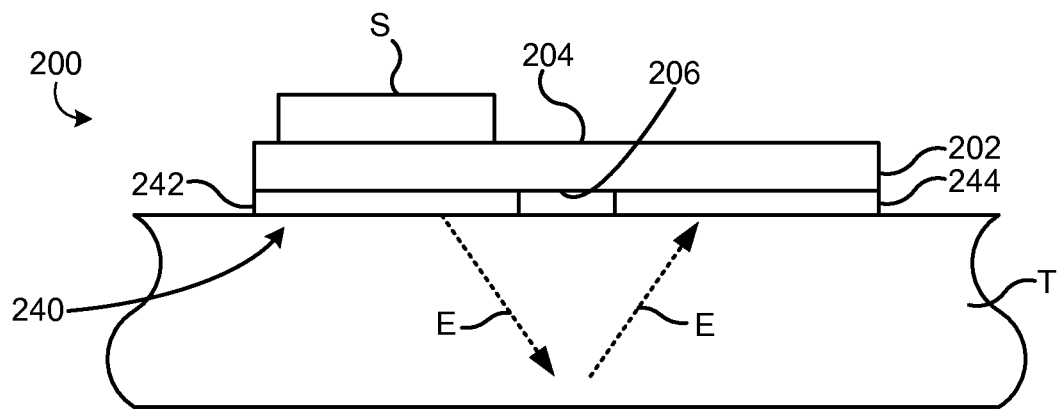
FIGS. 7-8 are side views of the apparatus of FIG. 2 coupled to an external stimulator and disposed on bodily tissue and delivering an electrical current to the bodily tissue and to an implanted conductive lead, respectively.
Figure 8:
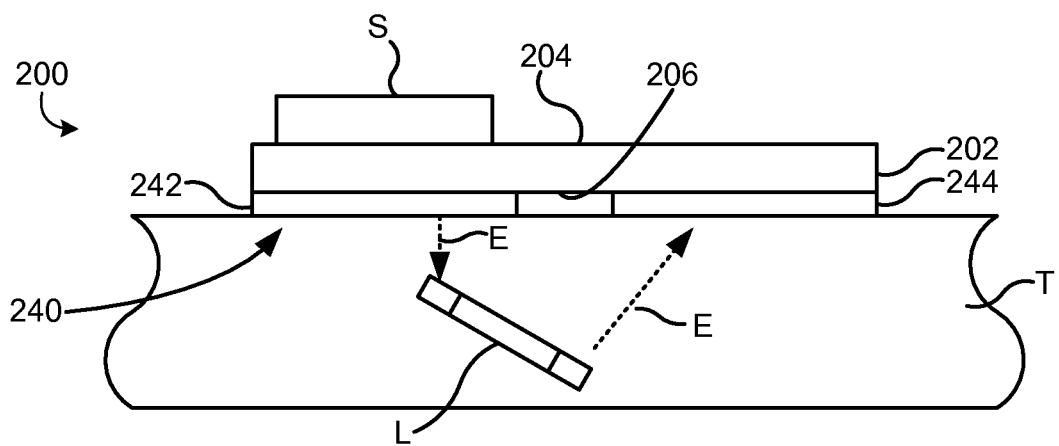

The electrode assembly 240 of the apparatus 200 is coupled to the second surface 206 of the PCB 202, as illustrated in FIG. 4. The electrode assembly 240 includes a first electrode 242 and a second electrode 244. As illustrated in FIGS. 7-8, each of the first electrode 242 and the second electrode 244 is configured to contact bodily tissue T and to facilitate transmission of an electrical current E through the bodily tissue, for example through subcutaneous bodily tissue located below and/or between the first electrode 242 and the second electrode 244. The first electrode 242 is configured to facilitate transmission of the electrical current E from the external stimulator S through the bodily tissue T. The first electrode 242 can facilitate transmission of the electrical current E to an electrical lead L at least partially implanted within the bodily tissue, as illustrated in FIG. 8. The second electrode 244 is configured to receive at least a portion of the electrical current E. As illustrated in FIGS. 7-8, for example, the second electrode 244 can receive electrical current E that has passed through the bodily tissue T and/or through an electrical lead L at least partially implanted within the bodily tissue. The transmission of current to an implanted lead is described, for example, in U.S. patent application Ser. No. 11/337,824, which is incorporated herein by reference in its entirety.

The electrodes 242, 244 are configured to adhere to bodily tissue (e.g., the skin) of the patient. Each electrode 242, 244 of the electrode assembly 240 includes a gel on the tissue-facing surface of the electrode. The gel can be any suitable known gel including, but not limited to, wet gels, karaya-gum-based hydrogels, and/or synthetic copolymer-based hydrogels. The first electrode 242 and second electrode 244 can be, for example, a cathodic gel electrode and an anodic gel electrode, respectively.

Figure 5:
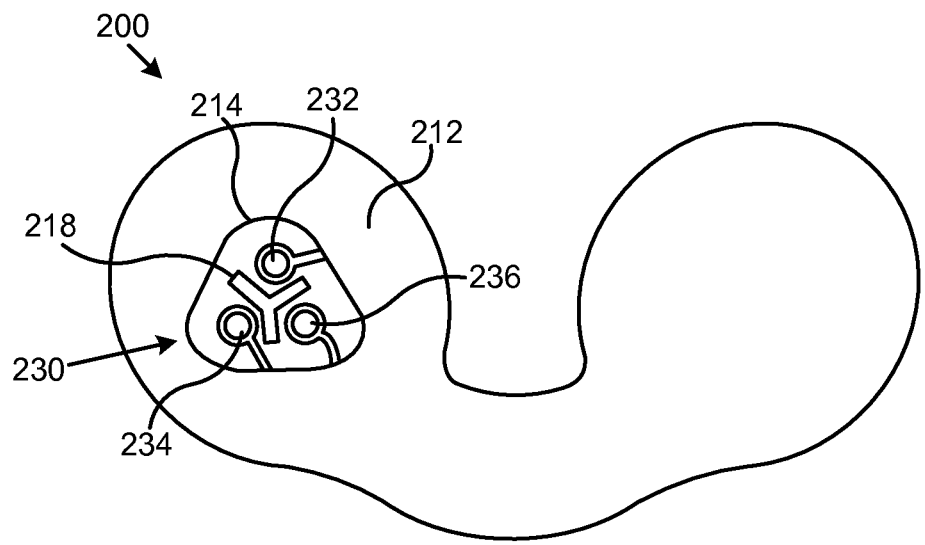
FIG. 5 is a top view of the apparatus of FIG. 2 with a portion of the apparatus in a covering.
Figure 6:
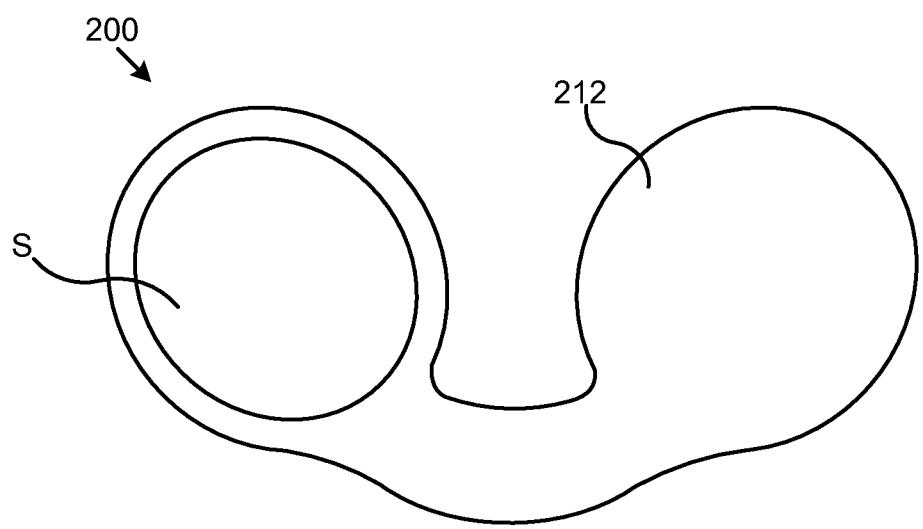
FIG. 6 is a top view of the apparatus of FIG. 5 coupled to an external stimulator.

As illustrated in FIG. 5, the apparatus 200 can be at least partially enclosed by a material 212, such as a material configured to increase the comfort of the patient utilizing the apparatus and/or protect components of the apparatus from external elements. The material at least partially encloses at least one of the first surface 204 of the PCB 202, the battery 220, and a portion of the electrical circuitry 250. The material 212 defines an opening 214 through which the connection assembly 230 is accessible. In this manner, the external stimulator S can be physically coupled to the apparatus 200 via the connection assembly 230, as illustrated in FIG. 6. The material 212 can be any suitable material including, for example, a foam, a water-proof material, plastic, an insulative material, a non-conductive material, a film, or the like, or any combination of the foregoing.

In use, a target bodily tissue is identified as the target for electrical stimulation. The apparatus 200 is positioned proximate to the identified target bodily tissue, such as on a surface of the patient's skin proximate to a subcutaneous target bodily tissue. For example, the apparatus 200 can be positioned proximate to an arm, leg, back, or other portion of the patient's body. The first and second electrodes 242, 244 are adhered to the patient's skin in the desired position.

The external stimulator S is placed in electrical communication with the battery 220 of the apparatus 200. The external stimulator S is electrically coupled to the battery 220 by coupling the external stimulator to the connectors 232, 234. The battery 220 provides power to the external stimulator S. In response to receiving power from the battery 220, the external stimulator S generates an electrical current and transmits the electrical current to the apparatus 200 via at least one connector 232, 234, 236. The electrical current is transmitted via the electrical circuitry 250 to the first electrode 242. The first electrode 242 transmits at least a portion of the electrical current E through the bodily tissue of the patient, as illustrated in FIG. 7. In some embodiments, as illustrated in FIG. 8, a portion of the electrical current E transmitted from the first electrode 242 through the bodily tissue is picked by a proximal end portion of an electrical conductor L (or lead) at least partially implanted within the bodily tissue, as illustrated in FIG. 8. The electrical conductor L is configured to transmit a portion of the electrical current E from its proximal end portion to a distal end portion of the electrical conductor L.

The electrical current E is transmitted from the distal end portion of the electrical conductor L through the bodily tissue T to the second electrode 244. At least a portion of the electrical current E is received by the second electrode 244. The electrical circuitry 250 transmits the electrical current E to at least one of the battery 220 or the external stimulator S to complete one cycle of electrical stimulation of the target bodily tissue. The cycle of electrical stimulation of the target bodily tissue is repeated as necessary. The apparatus 200 is disposable and can be removed from the patient and discarded when it is no longer needed or suitable for treatment, such as, for example, when a prescribed course of treatment is completed or when the battery is exhausted.

Although the substrate 202 has been illustrated and described as being a PCB, in other embodiments, the substrate can be constructed of a different material. For example, the substrate can be constructed of silicon, polyamide, or another suitable polymer, or any combination of the foregoing.

Furthermore, although at least a portion of the electrical circuitry 250 and/or the connection assembly 230 has been illustrated and described as being a conductive ink printed on a surface of the substrate 202, in other embodiments, at least one of the electrical circuitry and the connection assembly can be differently constructed. For example, the connection assembly can include a connector that is a wire, an antenna, a metal electrode, or the like. In another example, at least a portion of electrical circuitry can include or be a wire or another electrically conductive material.

Although the material 212 is illustrated as at least partially enclosing at least one of the first surface 204 of the PCB 202, the battery 220, and a portion of the electrical circuitry 250, in other embodiments, a material can be disposed over a different portion of the apparatus 200. For example, in some embodiments, the material can be an insulative film disposed over a portion of the electrical circuitry.

Although the apparatus 200 has been illustrated and described as being adhered to the body of the patient via adhesive gel electrodes, in other embodiments, an apparatus can be coupled to the patient with a tape, a strap, a band, a glue, or another adhesive, or any combination of the foregoing. Furthermore, an apparatus that includes a glue, another adhesive, or the like, to adhere to the patient can include the glue, other adhesive, or the like on all or a portion of the portion of the apparatus contacting the body of the patient.

Figure 9A:
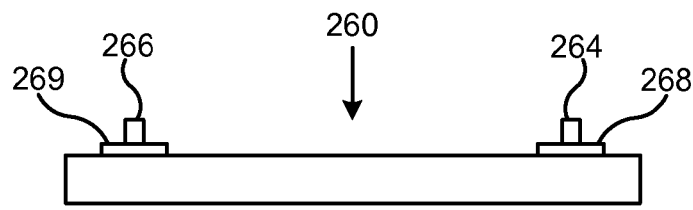
FIGS. 9A-9C are side views of portions of apparatus according to embodiments.
Figure 9B:
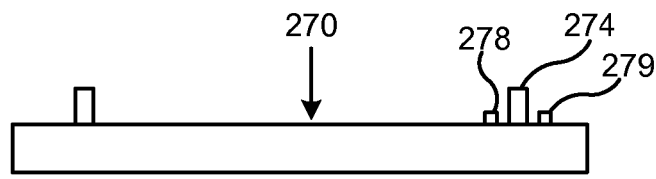
Figure 9C:
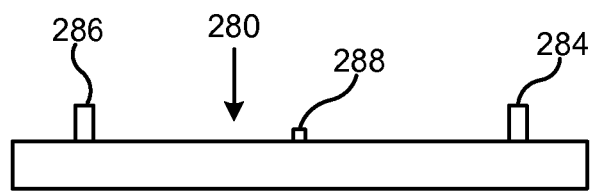

Although the apparatus 200 has been illustrated and described as having a connection assembly 230 including a Y-shaped hydrophobic barrier 218, in other embodiments, an apparatus can include a barrier having a different configuration. For example, as illustrated in FIG. 9A, in some embodiments, an apparatus 260 can include a barrier 268, 269 disposed about at least a portion of at least one connector 264, 266. In another example, in some embodiments, as illustrated in FIG. 9B, an apparatus 270 can include a plurality of barriers 278, 279 positioned at least on opposing sides of at least one connector 274. In still another example, as illustrated in FIG. 9C, in some embodiments, an apparatus can include a non-Y-shaped barrier 288 positioned between at least a first connector 284 and a second connector 286.

Figure 10:
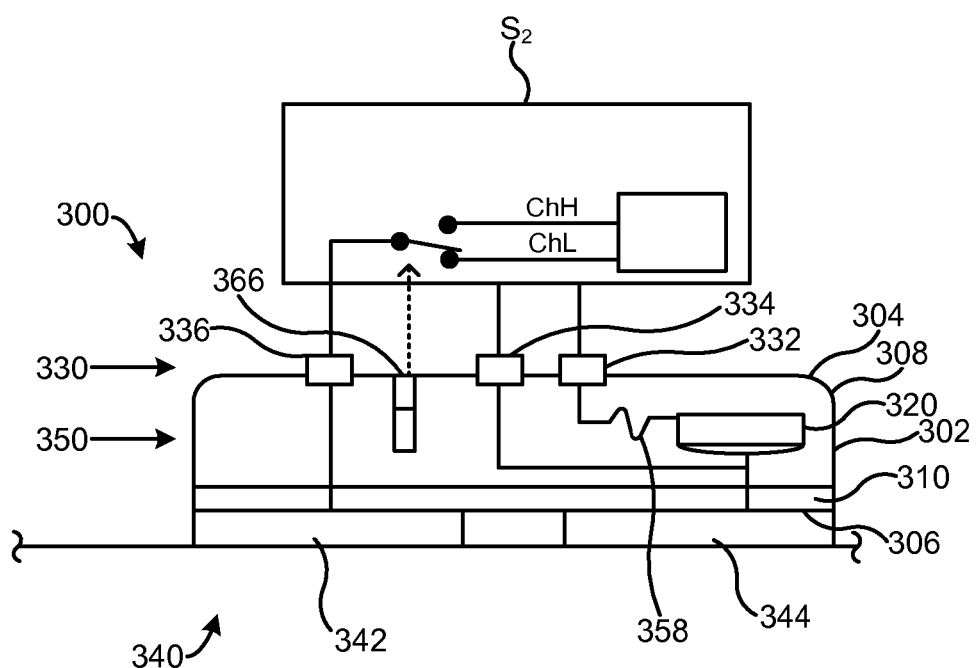
FIGS. 10-14 are side views of an apparatus according to embodiments and an external stimulator.

FIG. 10 is an illustration of an apparatus 300 according to an embodiment. The apparatus 300 is configured to transmit an electrical current from an external stimulator $S_2$ to a target bodily tissue. The apparatus includes a substrate 302, a power source 320, three connectors 332, 334, 336, electrical circuitry 350, and an electrode assembly 340.

The substrate 302 includes a first layer 308 having a first surface 304 and a second layer 310 having a second surface 306 different than the first surface. As illustrated in FIG. 10, each of the power source 320, the connectors 332, 334, 336, and the electrical circuitry 350 is at least partially embedded in the first layer 308 of the substrate 302. The first layer 308 of the substrate is formed of a first material. The second layer 310 of the substrate is formed over a portion of the electrode assembly 350. The second layer 310 of the substrate is formed of a second material different than the first material.

As illustrated in FIG. 10, the apparatus 300 includes a magnet 366 coupled to the substrate 302. The magnet 366 is configured to move a switch in the external stimulator from a first position in which the switch is electrically coupled to a first output channel to a second position in which the switch is electrically coupled to a second output channel different than the first output channel. For example, as illustrated in FIG. 10, movement of the magnet 366 from its first position can move the switch from a first position in which the switch is coupled to a high output channel (indicated as ChH) to a second position in which the switch is coupled to a low output channel (indicated as ChL). In this manner, the magnet 366 can be used to control an amount of electrical current output from the external stimulator $S_2$ to the apparatus 300.

Figure 11:
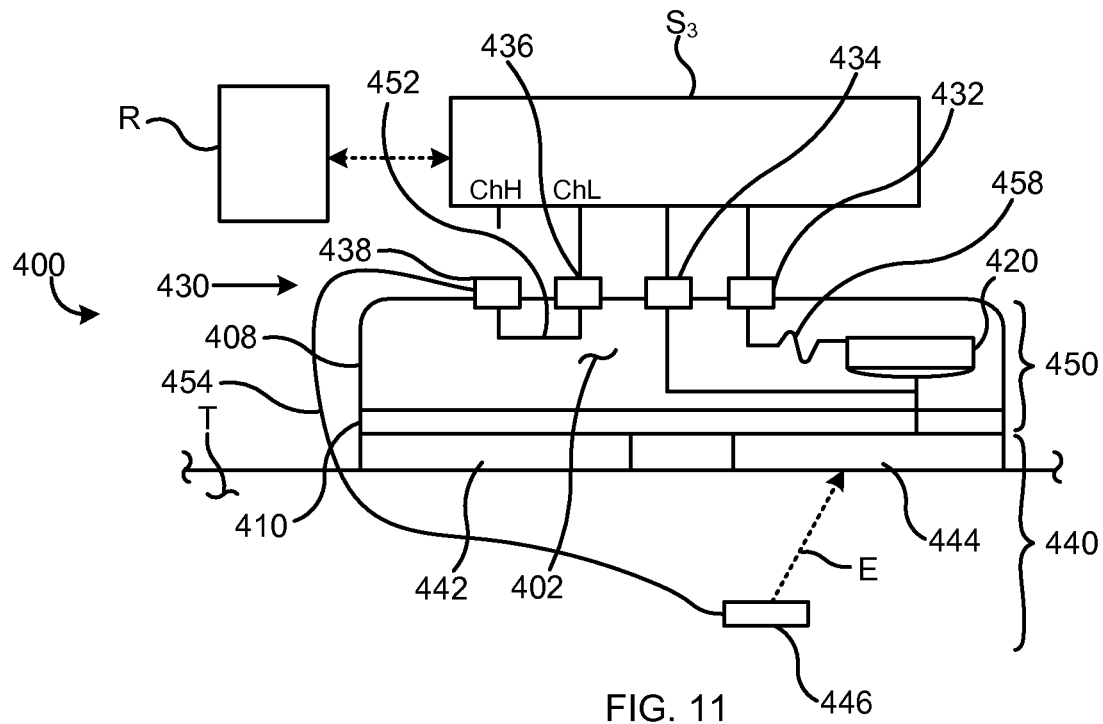

Although the apparatus 200, 300 have been illustrated and described as including at first electrode 242, 342 and a second electrode 244, 342 disposed on a second surface 206, 306 of a substrate 202, 302 and configured to facilitate transmission of an electrical current from an external stimulator S, $S_2$ through the bodily tissue, in some embodiments, an apparatus is configured to deliver or transmit the electrical current to the bodily tissue in a different manner. For example, as illustrated in FIG. 11, an apparatus 400 according to an embodiment is an electrode-battery assembly configured for percutaneous delivery of an electrical current to target bodily tissue.

The electrode-battery assembly 400 includes a substrate 402, a battery 420, a connection assembly 430, electrical circuitry 450, and an electrode assembly 440. The substrate 402 has a first layer 408 and a second layer 410. The battery 420, and electrical circuitry 450 are at least partially embedded in the first layer 408 of the substrate. The electrical circuitry 450 includes a fuse 458 configured to open the electrical circuit in the presence of a threshold electrical load, as described above.

An external stimulator $S_3$ is electrically coupled to the electrode-battery assembly 400 via the connection assembly 430. The connection assembly 430 includes a first connector 432, a second connector 434, a third connector 436, and a fourth connector 438. The connectors 432, 434, 436, 438 of the connection assembly 430 extend from a surface of the first layer 408 of the substrate 402.

The third connector 436 is configured to receive an electrical current input from the external stimulator $S_3$. The third connector 436 is configured to transmit the electrical current via a first electrical pathway 452 of the electrical circuitry 430 to the fourth connector 438. The fourth connector 438 is physically and electrically coupled to an electrode 446 of the electrode assembly 440 via a second electrical pathway 454. For example, as illustrated in FIG. 11, the fourth connector 438 is coupled to the second electrical pathway 454 including an electrical conductor exterior to the substrate 402 and extending from the fourth connector 438 to the electrode 446 implanted within the bodily tissue T.

The electrode assembly 440 includes a first electrode 442, a second electrode 444, and a third electrode 446. The first electrode 442 and second electrode 444 are coupled to the second layer 410 of the substrate 402. The third electrode 446 is coupled to the substrate 402 via the second electrical pathway 454 and is configured to be at least partially implanted within the bodily tissue T. At least the third electrode 446 is configured to transmit an electrical current from the external stimulator $S_3$ to the bodily tissue T. In use, the external stimulator $S_3$ transmits an electrical current to the third connector 436. The electrical current is transmitted from the third connector 436 via the first electrical pathway 452 to the fourth connector 438, and from the fourth connector via the second electrical pathway 454 to the third electrode 446. The third electrode 446 transmits at least a portion of the electrical current E to the bodily tissue, as illustrated in FIG. 11. The second electrode 444 is configured to receive at least a portion of the electrical current from the bodily tissue.

The electrode-battery assembly 400 is configured to receive an electrical current from the external stimulator $S_3$ via at least one of a first output channel and a second output channel of the external stimulator. For example, as illustrated in FIG. 11, the external stimulator $S_3$ has a high output channel ChH and a low output channel ChL. The electrode-battery assembly 400 is illustrated in FIG. 11 as being electrically coupled to the low output channel ChL of the external stimulator $S_3$ via the third connector 436, however, in use, a patient or practitioner operating the stimulator can selectively electrically couple the electrode-battery assembly to the high output channel ChH via the third connector.

The external stimulator $S_3$ can be wirelessly controlled by the operator. For example, the operator can wirelessly control the external stimulator $S_3$ using a remote control R to communicate with the stimulator over a radio frequency. In this manner, the operator can wirelessly program the external stimulator $S_3$, power on and/or off the external stimulator $S_3$, and/or select the desired output channel (e.g., ChH and/or ChL).

Although the apparatus 400 is illustrated and described as percutaneously transmitting the electrical current, in some embodiments, an apparatus is configured for both transcutaneous and percutaneous transmission of the electrical current. For example, an apparatus can be configured to transcutaneously transmit the electrical current through bodily tissue from a first electrode disposed on a surface of the patient's skin and percutaneously transmit the electrical current via a second electrode (e.g., similar to electrode 446 described above) at least partially implanted in the bodily tissue. In some embodiments, the high output channel ChH of the external stimulator is configured for transcutaneous stimulation and the low output channel ChL is configured for percutaneous stimulation of the target bodily tissue. Electrical current from each of the first electrode and the second electrode can be received by a third electrode disposed on the skin of the patient, similar to electrode 444 described above.

Figure 12:
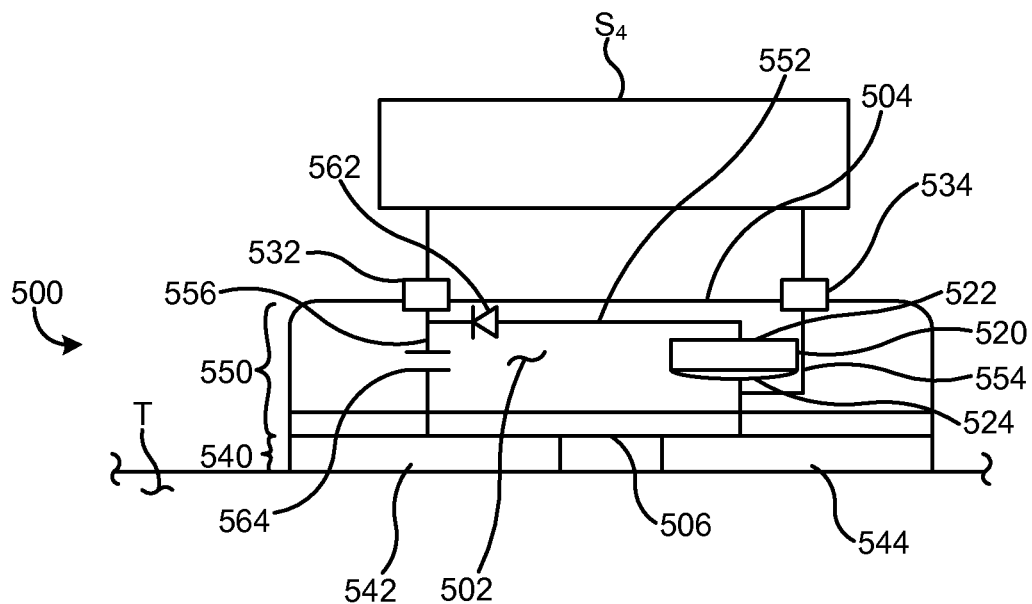

Although the apparatus 200, 300, 400 described above have been illustrated and described as including a fuse 258, 358, 458 configured to open the electrical circuit, in other embodiments, an apparatus 500 includes electrical circuitry differently configured to prevent a short circuit of the electrical circuit, as illustrated in FIG. 12. The apparatus 500 is configured to transmit an electrical stimulation to a bodily tissue and includes a substrate 502, an electrode assembly 540, a power source 520, and a connection assembly 530.

The substrate 502 has a first surface 504 and a second surface 506 different than the first surface. The power source 520 is coupled to the substrate 502 and can be any suitable source of power described herein. The power source 520 has a positive terminal 522 and a negative terminal 524. The power source 520 is configured to provide power to an external stimulator $S_4$, for example, when the external stimulator is in electrical communication with the power source.

The electrode assembly 540 is coupled to the second surface 506 of the substrate 502. The electrode assembly 540 is configured to facilitate transmission of an electrical current from the external stimulator $S_4$ through the bodily tissue. The electrode assembly includes a first electrode 542 and a second electrode 544 different than the first electrode.

The connection assembly 530 is coupled to the substrate 502 and includes up to two connectors configured to be in electrical communication with the external stimulator $S_4$. Specifically, as illustrated in FIG. 12, the connection assembly 530 includes a first connector 532 and a second connector 534. Each of the first connector 532 and a second connector 534 is coupled to the first surface 504 of the substrate 502. The first connector 532 is configured to electrically couple the external stimulator $S_4$ to the positive terminal 522 of the power source 520 and to the first electrode 542. The second connector 534 is configured to electrically couple the external stimulator $S_4$ to the negative terminal 524 of the power source 520 and to the second electrode 544.

The connection assembly 530 has a first configuration in which the two connectors 532, 534 are electrically coupled to the external stimulator $S_4$ (as illustrated in FIG. 12) and a second configuration in which the two connectors are electrically isolated from the external stimulator (not shown). When the connection assembly 530 is in its first configuration, the connection assembly completes a power circuit between the power source 520 and the external stimulator $S_4$ and a stimulation circuit between the external stimulator and the electrode assembly 540, as described in more detail herein.

The power circuit includes electrical circuitry 550, a diode 562, the connection assembly 530, and the power source 520. As illustrated in FIG. 12, the electrical circuitry 550 includes a first electrical pathway 552 and a second electrical pathway 554, each coupled to the substrate 502. The first electrical pathway 552 electrically couples the first connector 532 to the positive terminal 522 of the power source 520. The second electrical pathway 554 electrically couples the second connector 534 to the negative terminal 524 of the power source 520. When the connection assembly 530 is in its second configuration, the power circuit is open (or incomplete). When the connection assembly 530 is in its first configuration such that the first and second connectors 532, 534, respectively, are electrically coupled to the external stimulator $S_4$, the power circuit is closed (or complete) and the power source 520 provides power to the external stimulator.

The diode 562 is coupled to the substrate 502 and is disposed within the first electrical pathway 552. The diode 562 is configured to allow electrical current to flow in a first direction and to substantially inhibit flow of the electrical current in a second direction different than the first direction. As illustrated in FIG. 12, the diode 562 is configured to allow flow of the electrical current from the power source in a first direction towards the first electrode 542 via the first electrical pathway 552. The diode 562 is configured to substantially inhibit flow of the electrical current in a second direction opposite the first direction, such as from the first connector 532 to the power source 520 and/or to the second electrode 544 via the first electrical pathway 552. In this manner, the diode 562 is configured to prevent a short circuit of the electrical circuit because the stimulating electrical current transmitted from the external stimulator $S_4$ to the first connector 532 is substantially inhibited from flowing to the power source 520, which otherwise may cause the power source to overheat, explode, or otherwise become defective.

The stimulation circuit includes electrical circuitry 550, a capacitor 564, the connection assembly 530, and the electrode assembly 540. As illustrated in FIG. 12, the electrical circuitry 550 includes a third electrical pathway 556 coupled to the substrate 502. The third electrical pathway 556 electrically couples the first connector 532 to the first electrode 542 of the electrode assembly 540. The second electrical pathway 554 electrically couples the second connector 534 to the second electrode 544. As such, the negative terminal 524 of the power source 520 is also coupled to the second electrode 544.

The capacitor 564 is coupled to the substrate 502 and is disposed in the electrical circuitry 550, for example, in the third electrical pathway 556 as illustrated in FIG. 12. The capacitor 564 is configured to separate an alternating current from a direct current. The capacitor 564 is configured to substantially inhibit flow of the direct current from the power source 520 to the first electrode 542. The capacitor 564 is configured to deliver at least one of the alternating current and the direct current from the external stimulator to the first electrode.

When the connection assembly 530 is in its first configuration (and the power circuit is closed, as described above), the stimulation circuit is also closed and an electrical current can be transmitted from the external stimulator through the target bodily tissue via the apparatus 500. Specifically, the electrical current is transmitted from the external stimulator $S_4$ to the first connector 532. The first connector 532 transmits the electrical current towards the first electrode 542 via the third electrical pathway 556. The capacitor 564 separates direct current from alternating current, and then transmits at least one of the direct current or the alternating current to the first electrode 542. The first electrode 542 transmits the electrical current through the bodily tissue T. The second electrode 544 receives at least a portion of the electrical current from the bodily tissue T and transmits the electrical current to the electrical circuitry 550 of the apparatus 500.

Although the diode 562 has been illustrated and described as being configured to allow flow of the electrical current from the power source 520 in a first direction towards the first electrode 542 and to substantially inhibit flow of the electrical current in a second direction opposite the first direction, such as from the first connector 532 to the power source 520 and/or to the second electrode 544 via the first electrical pathway 552, in some embodiments, the diode 562 is configured to allow flow of the electrical current in the second direction and to substantially inhibit flow of the electrical current in the first direction.

Figure 13:
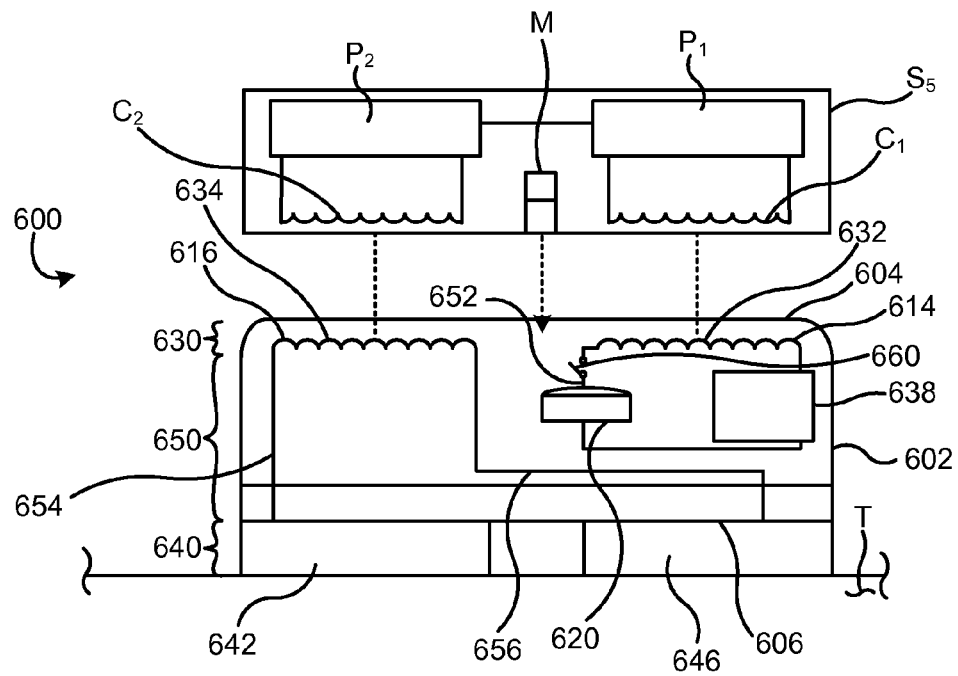

Although the apparatus 500 has been illustrated and described as being electrically coupled to the external stimulator via the two mechanical connectors 532, 534, in some embodiments, an apparatus is electrically coupled to the external stimulator in a different manner. For example, as illustrated in FIG. 13, in some embodiments, an apparatus 600 is wirelessly electrically coupled to an external stimulator $S_5$.

The apparatus 600 includes a substrate 602 configured to be positioned on or proximate to the bodily tissue. The substrate 602 has a first surface 604 and a second surface 606 different than the first surface. The second surface 606 of the substrate is configured to face the bodily tissue and the first surface 604 is configured to face away from the bodily tissue when the apparatus is positioned on or proximate to the bodily tissue. A power source 620 is coupled to the substrate 602. As illustrated in FIG. 13, the power source 620 is at least partially embedded in the substrate 602.

The apparatus 600 includes a connection assembly 630 configured to be in electrical communication with an external stimulator $S_5$. The connection assembly 630 includes a first connector 632 and a second connector 634. Each of the first connector 632 and the second connector 634 is an antenna configured as a first coil 614 and a second coil 616, respectively, that is configured to be in wireless electrical communication with the external stimulator $S_5$. The first coil 614 and second coil 616 are each coupled to the first surface 604 of the substrate 602. Specifically, the coils 614, 616 are embedded in the substrate 602. In this manner, the coils 614, 616 are configured to prevent a short circuit of the electrical circuit, for example, by substantially preventing exposure of the coils to a fluid.

The connection assembly 630 has a first configuration in which the coils 614, 616 are electrically coupled to the external stimulator $S_5$ and a second configuration in which the coils are electrically isolated from the external stimulator. The connection assembly 630 is configured to complete a power circuit between the power source 630 and the external stimulator $S_5$ and a stimulation circuit between the external stimulator and an electrode assembly 640, as described in more detail herein.

As illustrated in FIG. 13, the power circuit includes the first coil 614, the power source 620, an oscillator 638, and electrical circuitry 650. The electrical circuitry 650 includes a switch 660 disposed in a first electrical pathway 652. The switch 660 can be any suitable switch for opening and closing a circuit. For example, the switch 660 can be a reed switch including a pair of contacts on ferrous metal reeds in a hermetically sealed glass envelope (not shown). The switch 660 has an open configuration (see, e.g., FIG. 13) and a closed configuration. In its open configuration, the pair of contacts of the reeds is open (or separate). Thus, the electrical circuit is open when the switch is in its open configuration. The switch 660 is movable to its closed configuration by the introduction of a magnetic field, such as by placing a magnet M in the external stimulator $S_5$ proximate to the switch. Specifically, the presence of the magnetic field causes the pair of contacts to close or otherwise come together. As such, the switch 660 is configured to close the electrical circuit when the switch is moved to its closed configuration. The switch 660 is biased to its open configuration. In this manner, the electrical circuitry is configured to prevent a short circuit of the electrical circuit.

The power source 620 is configured to transmit an electrical current to the electrical circuitry 650 when the connection assembly 630 is in its first configuration and the switch 660 is in its closed configuration. The electrical circuitry 650 is configured to transmit the electrical current to the oscillator 638. The oscillator 638 is configured to deliver at least one oscillation (of electrical current) to the first coil 614 to initiate wireless transmission of an electrical output from the first coil to the external stimulator $S_5$. The first coil 614 is configured to wirelessly transmit the electrical output to the external stimulator $S_5$, such as to a coil $C_1$. The coil $C_1$ of the external stimulator $S_5$ can transmit the electrical current to a source of power $P_1$ disposed within the external stimulator. The source of power $P_1$ can transmit the electrical current to a stimulation circuit and/or a radio frequency circuit coupled to the external stimulator $S_5$. For example, the source of power $P_1$ can transmit the electrical current to a portion of the stimulation circuit $P_2$ disposed on the external stimulator $S_5$.

As illustrated in FIG. 13, the stimulation circuit includes the second coil 616, electrical circuitry 650, and an electrode assembly 640. The second coil 616 is disposed proximate to the first surface 604 of the substrate 602. Specifically, the second coil 616 is embedded in the substrate 602 proximate the first surface 604. The second coil 616 is configured for wireless electrical communication between an electrode of the electrode assembly 640 and the external stimulator $S_5$. For example, the second coil 616 is configured to receive an electrical input from a coil $C_2$ of the external stimulator $S_5$ and to transmit at least a portion of the electrical input (or current) to the electrical circuitry 650.

The electrical circuitry 650 is configured to transmit the electrical current to the electrode assembly, for example, via a second electrical pathway 654. The electrode assembly 640 is coupled to the second surface 606 of the substrate 602 and includes a first electrode 642 and a second electrode 644 different than the first electrode. The first electrode 642 is coupled to the second electrical pathway 654 of the electrical circuitry 650. The first electrode 642 can receive an electrical current from the electrical circuitry 650 via the second electrical pathway 654 and can facilitate transmission of the electrical current through the bodily tissue. The second electrode 644 is configured to receive a portion of the electrical current from the bodily tissue. The second electrode 644 is configured to transmit the electrical current to the electrical circuitry 650, such as to a third electrical pathway 656. The electrical circuitry 650 can transmit the electrical current to the second coil 616. The second coil 616 can wirelessly transmit an electrical output to the external stimulator $S_5$.

Although the apparatus 600 is illustrated and described as being in wireless communication with the external stimulator $S_5$ via a connection assembly 630 including the first and second coils 614, 616, respectively, in some embodiments, an apparatus is in wireless communication with an external stimulator via a connection assembly having a different configuration. For example, in some embodiments, an apparatus includes at least one antenna configured to wirelessly communicate with an external stimulator.

Figure 14:
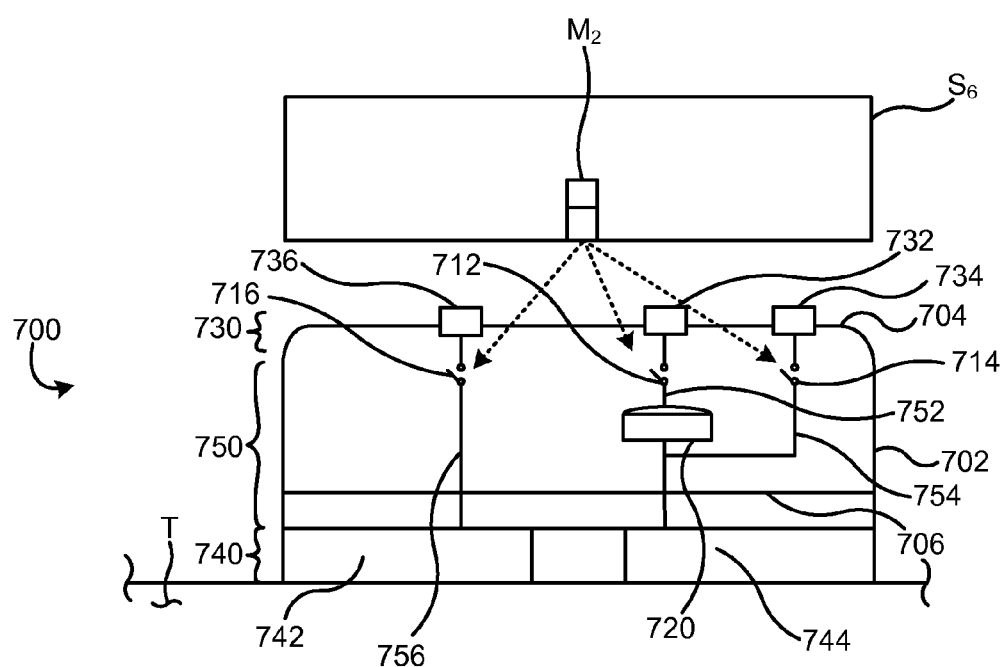

As illustrated in FIG. 14, an apparatus 700 includes a connection assembly 730 having a plurality of connectors that includes a first connector 732, a second connector 734, and a third connector 736. The connection assembly 730 is disposed proximate to a first surface 704 of a substrate 702. Each of the first connector 732, second connector 734, and third connector 736 is configured to be coupled to the a counterpart connector (not shown) on the stimulator $S_6$. The first connector 732 is configured to be in electrical communication with a battery 720 coupled to the substrate 702 via a first electrical pathway 752 of electrical circuitry 750. The first electrical pathway 752 includes a first switch 712. The second connector 734 is configured to be in electrical communication with the battery 720 via a second electrical pathway 754. The second connector 734 is also configured to be in electrical communication with a first electrode 746 of an electrode assembly 740 coupled to the substrate 702 via the second electrical pathway 754. The second electrical pathway 754 includes a second switch 714. The third connector 736 is configured to be in electrical communication with a second electrode 742 of the electrode assembly 740 via a third electrical pathway 756. The third electrical pathway 756 includes a third switch 716. Each switch 712, 714, 716 is configured to move from an open configuration to a closed configuration in the presence of a magnetic field. For example, as illustrated in FIG. 14, each switch 712, 714, 716 is configured to move to its respective closed configuration by a magnet $M_2$ coupled to the external stimulator $S_6$. When the switches 712, 714, 716 are each in the closed configuration, and the external stimulator $S_6$ is in electrical communication with the connection assembly 730, the electrical circuit is complete (or closed).

When the electrical circuit is complete, the battery 720 is configured to provide power to the external stimulator $S_6$. Power from the battery 720 enables the external stimulator to generate an electrical output to be received as an electrical input by the third antenna 736. The second electrode 742 is configured to receive the electrical current from the third antenna 736 via the third electrical pathway 756. The second electrode 742 is configured to transmit the electrical current through target bodily tissue T. The first electrode 744 is configured to receive at least a portion of the electrical current from the bodily tissue T and to transmit the electrical current to the external stimulator $S_6$ via the second electrical pathway 754.

Although the apparatus 600, 700 have been illustrated and described as including two antenna coils 614, 616 and three connectors 732, 734, 736, respectively, in other embodiments an apparatus can include any suitable combination of connectors, e.g., wired and/or wireless, for electrical communication with an external stimulator.

Figure 15:
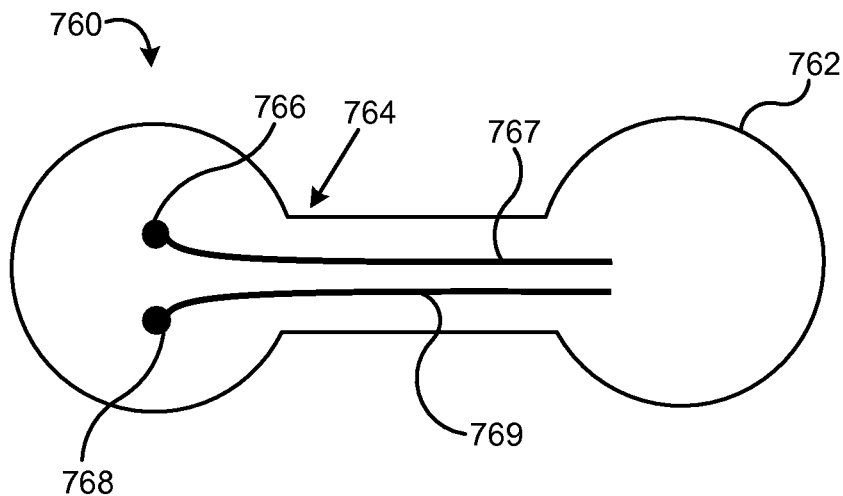
FIGS. 15-18 are top views of an antenna of an apparatus according to embodiments.

In some embodiments, as illustrated in FIG. 15, an apparatus 760 includes a planar dipole antenna 764 that is printed onto a substrate 762, such as a PCB. The antenna 764 includes a first connector 766, a first branch 767, a second connector 768, and a second branch 769. The first connector 766 is configured to be in electrical communication with an external stimulator (not shown) The first branch 767 is configured to electrically couple the first connector 766 to electrical circuitry (not shown) coupled to the substrate 762. The second connector 768 is configured to be in electrical communication with the external stimulator. The second branch 769 is configured to electrically couple the first connector 768 to the electrical circuitry.

Figure 16:
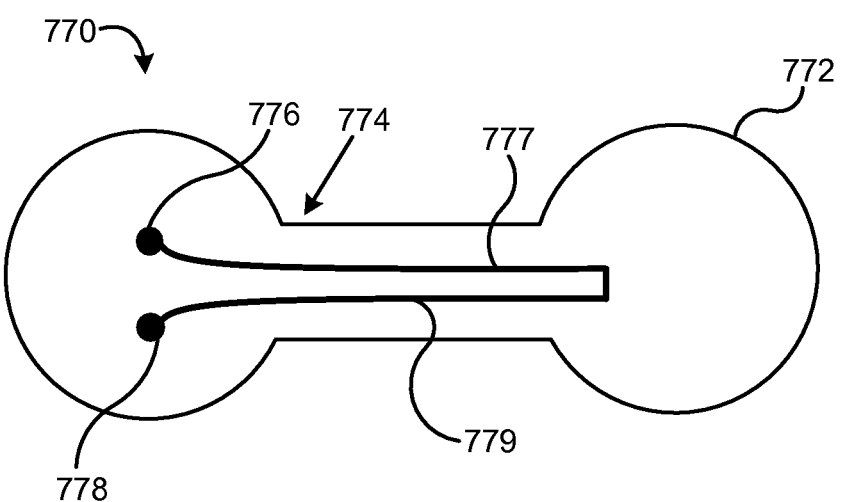

In some embodiments, as illustrated in FIG. 16, an apparatus 770 includes a planar folded dipole antenna coupled to a substrate 772. The antenna 774 includes a first connector 776, a first branch 777, a second connector 778, and a second branch 779. The first connector 776 is configured to be in electrical communication with an external stimulator (not shown). The first branch 777 is configured to electrically couple the first connector 776 to electrical circuitry (not shown) coupled to the substrate 772. The second connector 778 is configured to be in electrical communication with the external stimulator. The second branch 779 is configured to electrically couple the second connector 778 to the electrical circuitry.

Figure 17:
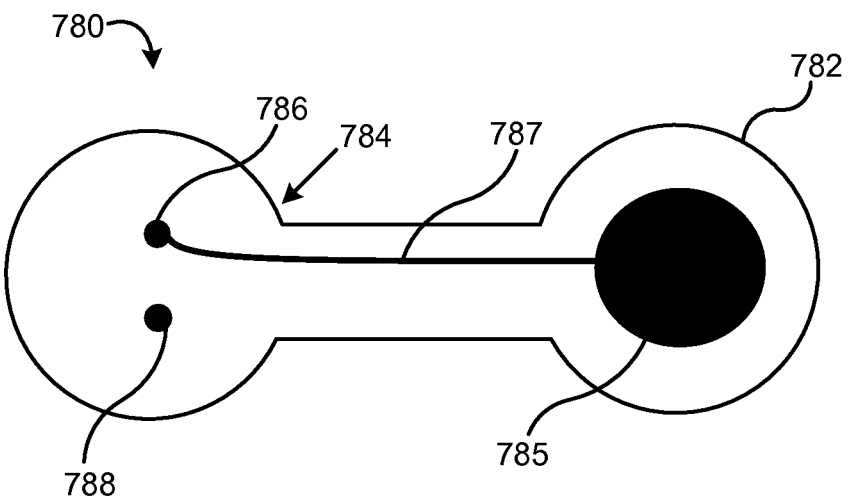

In yet another example, in some embodiments, as illustrated in FIG. 17, an apparatus 780 includes a planar non-symmetrical dipole antenna 784, which may also be referred to as a monopole antenna, coupled to a substrate 782. The antenna 784 includes a first connector 786 and a branch 787. The first connector 786 is configured to be in electrical communication with an external stimulator (not shown). The branch 787 is configured to electrically couple the first connector 786 and electrical circuitry (not shown) coupled to the substrate 782. The branch 787 can be coupled to a power source 785. The antenna 764 includes a second connector 788 configured to be in electrical communication with the external stimulator.

Figure 18:
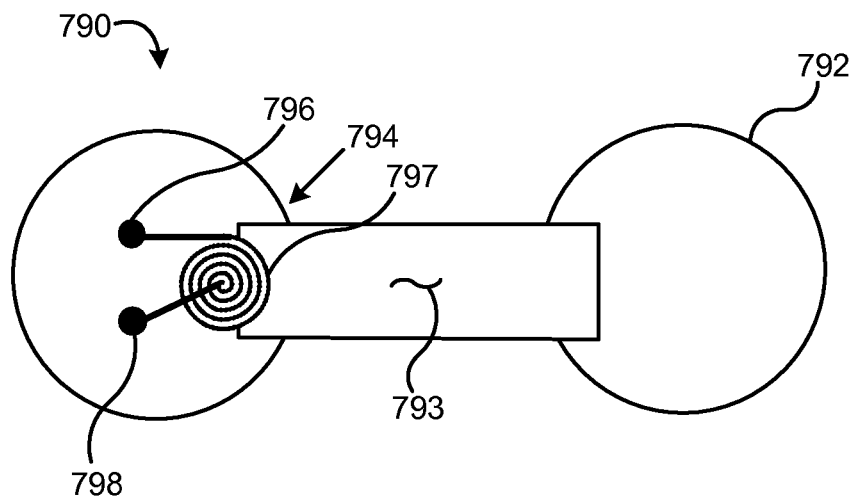

In still another example, in some embodiments, as illustrated in FIG. 18, an apparatus 790 includes a planar spiral antenna 794 coupled to a substrate 792, such as a PCB. The antenna 794 includes a first connector 796, a second connector 798, and an electrical pathway 797. Each of the first connector 796 and the second connector 798 is configured to be in electrical communication with an external stimulator (not shown). The electrical pathway 797 electrically couples the first connector 796 to the second connector 798. The electrical pathway 797 is configured as a spiral at least partially printed on a first surface 793 of the PCB 792. In some embodiments, a return electrical pathway (not shown) can be at least partially printed on an opposing surface (not shown)

of the PCB 792. In some embodiments, a return electrical pathway can be at least partially printed on an inner layer of a multi-layered PCB.

Although the apparatus 200, 300, 400, 500, 600, 700 have been illustrated and described as including a power source (or battery) 220, 320, 420, 520, 620, 720, respectively, coupled to a substrate 202, 302, 402, 502, 602, 702, respectively, in some embodiments, an apparatus includes a power source that is the substrate.

Figure 19:
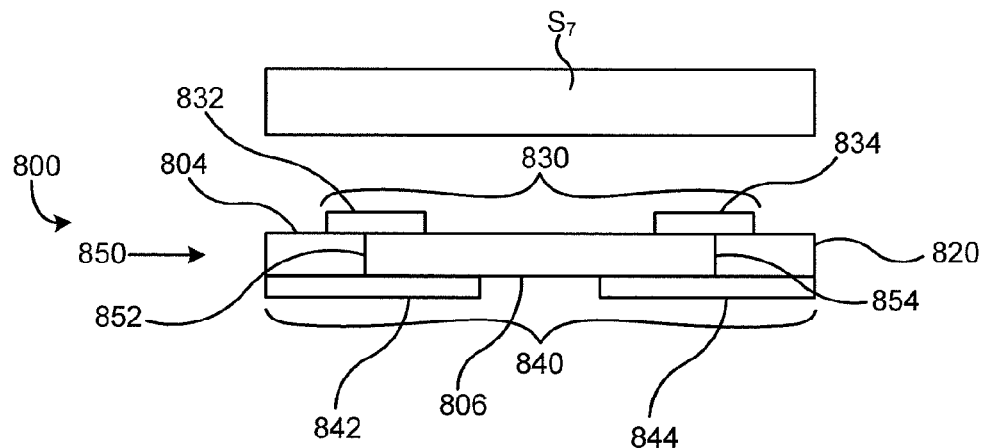
FIG. 19 is a side view of an apparatus according to an embodiment and an external stimulator.

For example, as illustrated in FIG. 19, an apparatus 800 includes a flexible battery 820 having a first surface 804 and a second surface 806. The flexible battery 820 is configured to provide power to an external stimulator $S_7$ coupled the flexible battery 820. The external stimulator $S_7$ can be coupled to the flexible battery by any coupling mechanism described herein that puts the external stimulator in electrical communication with the apparatus 800. For example, as illustrated in FIG. 19, the apparatus 800 includes a connection assembly 830 coupled to the first surface of the flexible battery 820. The connection assembly 830 is configured to complete a power circuit between the flexible battery 820 and the external stimulator $S_7$ and a stimulation circuit between the external stimulator an at least one electrode. The connection assembly 830 includes a first connector 832 and a second connector 834. Each connector 832, 834 is configured to electrically couple the flexible battery 820 to the external stimulator $S_7$. The first connector 832 is configured to electrically couple the external stimulator $S_7$ to a first electrode 842 of an electrode assembly 840 via electrical circuitry 850. The second connector 834 is configured to electrically couple the external stimulator $S_7$ to a second electrode 844 of the electrode assembly via the electrical circuitry 850. The electrode assembly 840 is coupled directly to the second surface 806 of the flexible battery 820. Each of the first electrode 842 and the second electrode 844 is configured to contact a bodily tissue.

In use, when the external stimulator $S_7$ is electrically coupled to the flexible battery 820, the flexible battery provides power to the external stimulator. The external stimulator $S_7$ transmits an electrical output to the first connector 832. The first connector 832 transmits the electrical input as an electrical current to the first electrode 842 via a first electrical pathway 852. The first electrode 842 transmits the electrical current through the bodily tissue to stimulate at least a portion of the bodily tissue. The second electrode 844 receives a portion of the electrical current from the bodily tissue. The second electrode 844 transmits the electrical current to the second connector 834 via a second electrical pathway 854. The second connector 834 transmits an electrical output to the external stimulator $S_7$.

The flexible battery 820 can be biodegradable. In some embodiments, for example, the flexible battery 820 can include a plurality of carbon nanotubes, cellulose disposed between at least a portion of a first carbon nanotube and a second carbon nanotube, an electrolyte, and/or a metal foil of lithium and ion.

While various embodiments have been described above, it should be understood that they have been presented by way of example only, and not limitation. Elements of each embodiment described herein may be combined in any suitable manner with one or more elements of another embodiment described herein. Where methods described above indicate certain events occurring in certain order, the ordering of certain events may be modified. Additionally, certain of the events may be performed concurrently in a parallel process when possible, as well as performed sequentially as described above.

For example, although apparatus 200 is illustrated and described as including a fuse 258, in some embodiments, an apparatus similar to apparatus 200 may include a switch similar to switch 660 in addition to or instead of a fuse.

Although an apparatus has been illustrated and described herein as including one switch or three switches, in other embodiments, an apparatus can include any suitable number of switches, such as two, four, or more switches.

Although a switch has been illustrated and described herein as being in an open configuration in the absence of a magnetic field and as being in a closed configuration in the presence of a magnetic field, in other embodiments, the switch can be differently configured. For example, in some embodiments, a switch can be configured to be in a closed configuration in the absence of a magnetic field and an open configuration in the presence of a magnetic field.

In another example, although an apparatus has been illustrated and described herein as having mechanical connectors for connection to the external stimulator, in other embodiments, such an apparatus can include a wireless connector.

In still another example, although the apparatus have been illustrated and described as including two electrodes, in other embodiments, an apparatus can include any suitable number of electrodes. For example, in some embodiments, an apparatus includes a first cathodic electrode and a plurality of anodic electrodes. The plurality of anodic electrodes can include two, three, four, or more electrodes. Each electrode of the plurality of anodic electrodes can be selectively positioned at a desired location on the body of the patient, such as at spaced locations to help direct an electrical current from the cathodic electrode through a greater area of bodily tissue. In other embodiments, for example, an apparatus can include a first anodic electrode and a plurality of cathodic electrodes. The plurality of cathodic electrodes can transmit a plurality of electrical currents through the bodily tissue to the anodic electrode. In still other embodiments, an apparatus can include a plurality of cathodic electrodes and a plurality of cathodic electrodes.

Figure 20:
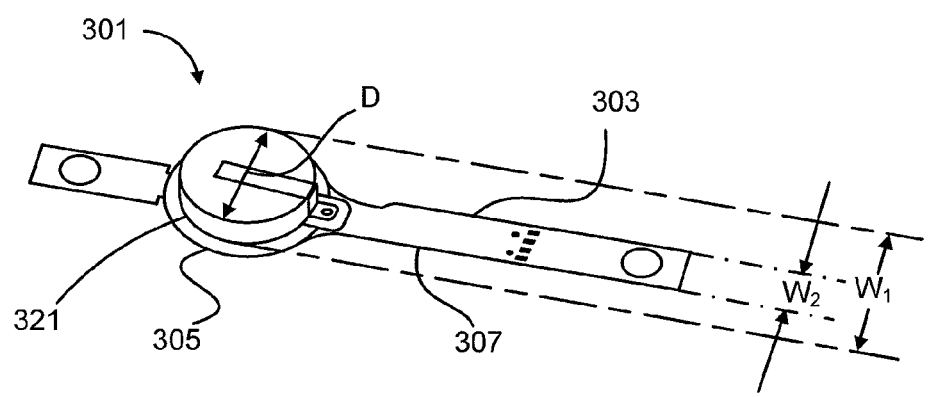
FIG. 20 is a perspective view of an apparatus according to an embodiment.

Although the apparatus have been illustrated and described as including a substrate having a length and a width greater than a length of a first diameter of the power source and a width of a second diameter of the power source, in other embodiments, an apparatus includes a substrate having a different configuration. For example, as illustrated in FIG. 20, an apparatus 301 can include a substrate 303 that has a first portion 305 having a width $W_1$ equal to or greater than a diameter D of the power source 321 and a second portion 307 having a width $W_2$ less than the width $W_1$ of the first portion 305 of the substrate 303.

In yet another example, although the connectors 232, 234, 236 of apparatus 200 have been illustrated and described as having a vertical orientation, in other embodiments, an apparatus can include at least one connector having a different orientation. For example, as illustrated in FIGS. 21-24, an apparatus 900 includes a substrate 902, a power source 920, a connection assembly 930, electronic circuitry 950, an electrode assembly 940, and a coupling mechanism 912 (not shown in FIGS. 21 and 22 for clarity of illustration purposes).

The connection assembly 930 includes connectors 932, 934, 936, 938. Each of the connectors 932, 934, 936, and 938 has a horizontal orientation. In other words, each of the connectors 932, 934, 936, and 938 has an orientation that is substantially parallel to a portion of the substrate 902. In this manner, the external stimulator $S_8$ is moved laterally to engage and/or disengage an external stimulator $S_8$ with the apparatus 900.

The connectors 932, 934, 936, 938 are electrically coupled to an electrical pathway 952, 954, 956, 958, respectively, of the electronic circuitry 950. The connectors 932, 934, 936, 938 are configured to electrically couple the electronic circuitry 950 to the external stimulator $S_8$ by being coupled to a counterpart connector $R_1$, $R_2$, $R_3$, $R_4$, respectively, of the external stimulator $S_8$ (see, e.g., FIG. 23).

Figure 24:
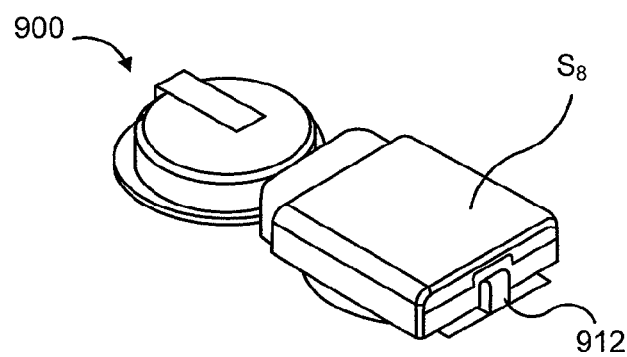
FIG. 24 is the apparatus of FIG. 21 and the external stimulator of FIG. 23.

The coupling mechanism 912 is configured to couple the external stimulator $S_8$ to the apparatus 900. As illustrated in FIG. 24, the coupling mechanism 912 is configured to engage a portion of the external stimulator $S_8$. For example, the external stimulator $S_8$ can define a groove or recess configured to receive a portion of the first member of the apparatus 900. Although the apparatus 900 is illustrated as having the connection assembly 930 coupled to an end of the external stimulator $S_8$ and the coupling mechanism 912 engaged with an opposite end of the external stimulator $S_8$, in other embodiments, the connection assembly and/or the coupling mechanism can engage a different portion of the external stimulator $S_8$.

Figure 25:
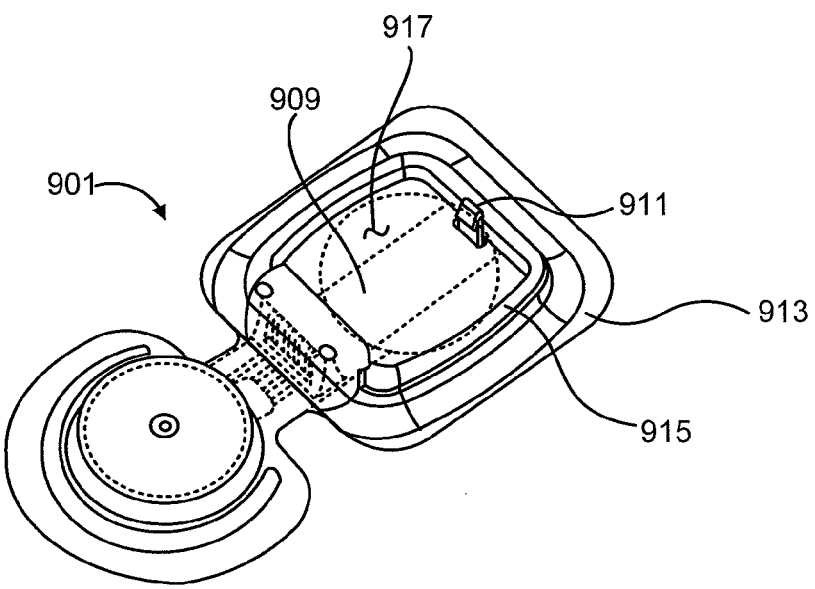
FIG. 25 is an apparatus according to an embodiment.
Figure 26:
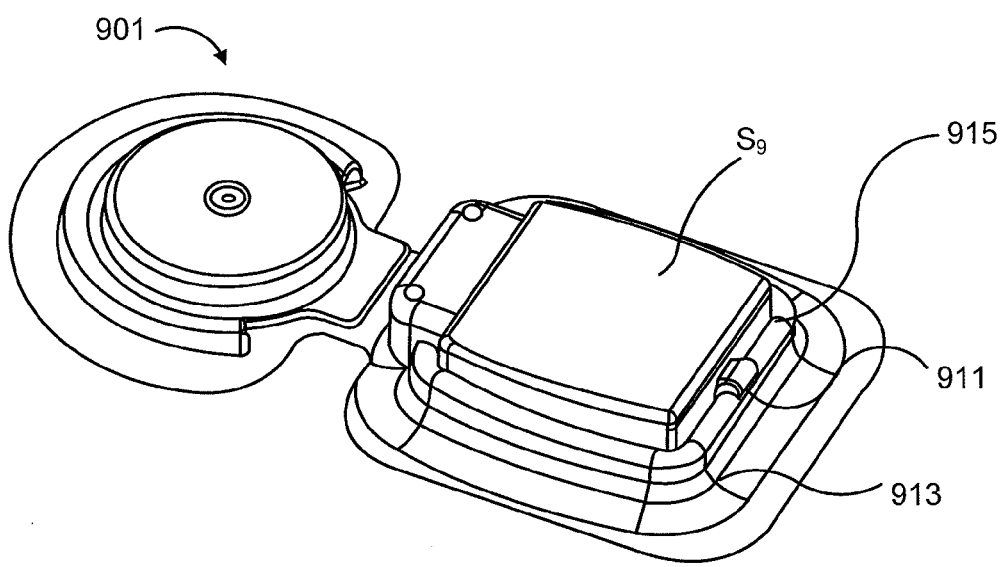
FIG. 26 is the apparatus of FIG. 25 and an external stimulator.

In some embodiments, as illustrated in FIGS. 25 and 26, an apparatus 901 includes a housing 913. The housing 913 is configured to at least partially enclose components (e.g., as shown dashed lines in FIG. 25) of the apparatus 901, such as, but not limited to, a power source, electronic circuitry, a substrate, or the like. The housing 913 defines a perimeter 915 and a recess 917 within the perimeter 915. The recess 917 is configured to at least partially receive an external stimulator $S_9$, as illustrated in FIG. 26. A coupling mechanism 909 (shown in dashed lines in FIG. 25) is configured to removably couple the external stimulator $S_9$ to the housing 913. The coupling mechanism 909 is coupled to the housing 913 and includes a protrusion 911. The protrusion 911 is configured to engage the external stimulator $S_9$ when the external stimulator $S_9$ is at least partially received in the recess 917. The protrusion 911 is configured to release the external stimulator $S_9$ when the protrusion 911 is pushed, depressed, or otherwise moved by the operator (e.g., a physician or the patient). In some embodiments, the protrusion 911 is configured to move the external stimulator $S_9$ in a direction away from the recess 917 when the protrusion 911 is pressed or moved by the operator.

Figure 27:
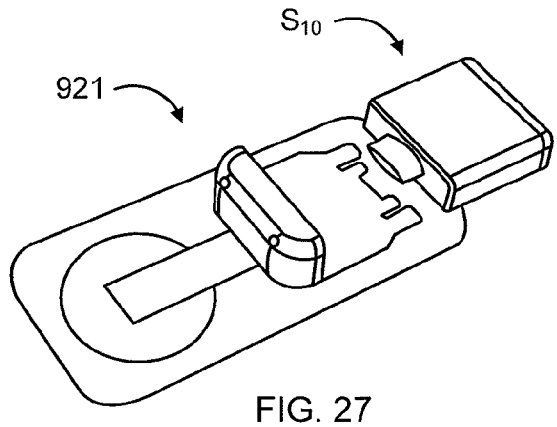
FIG. 27 is an apparatus according to an embodiment and an external stimulator.
Figure 28:
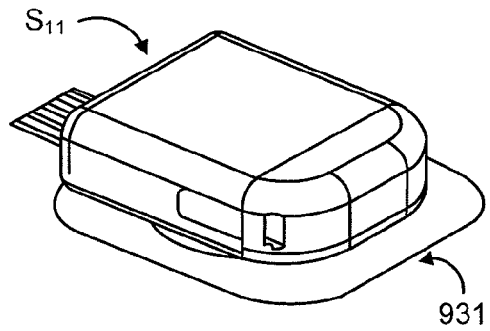
FIG. 28 is a portion of an apparatus according to an embodiment and an external stimulator.

Although the apparatus 900 is illustrated and described herein as including four horizontally oriented connectors 932, 934, 936, 938 configured to be coupled to the external stimulator $S_8$, in other embodiments, an apparatus 921, 931 can be configured to receive a horizontal protrusion of a external stimulator $S_{10}$, $S_{11}$, respectively, as illustrated in FIGS. 27 and 28.

Figure 29:
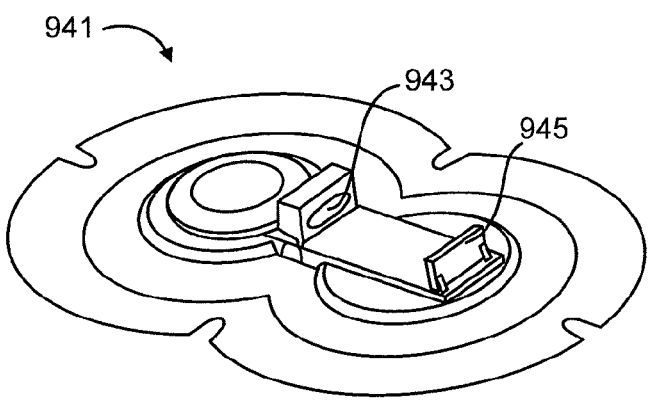
FIG. 29 is an apparatus according to an embodiment.
Figure 30:
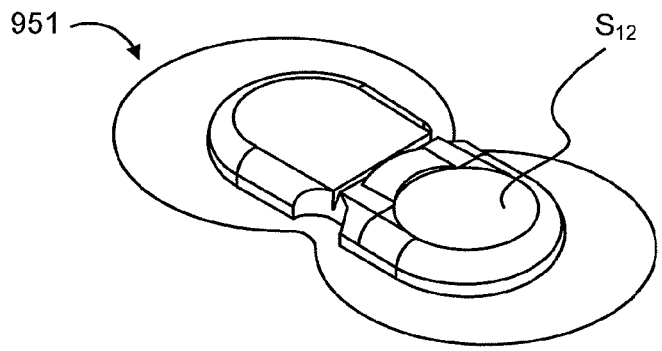
FIG. 30 is an apparatus according to an embodiment and an external stimulator.

In another embodiment, as illustrated in FIG. 29, an apparatus 941 includes a receiving portion 943 configured to receive a portion of an external stimulator $S_{12}$ (not shown) and a protrusion 945 configured to engage an outer surface of the external stimulator $S_{12}$. In still another embodiment, an apparatus 951 is configured to be coupled to an external stimulator $S_{12}$ without a protrusion, as illustrated in FIG. 30.

Figure 31:
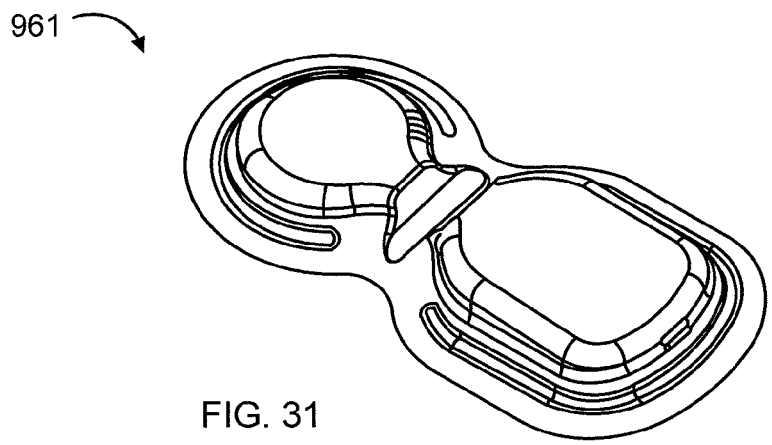
FIGS. 31-33 are apparatus according to embodiments and an external stimulator.
Figure 32:
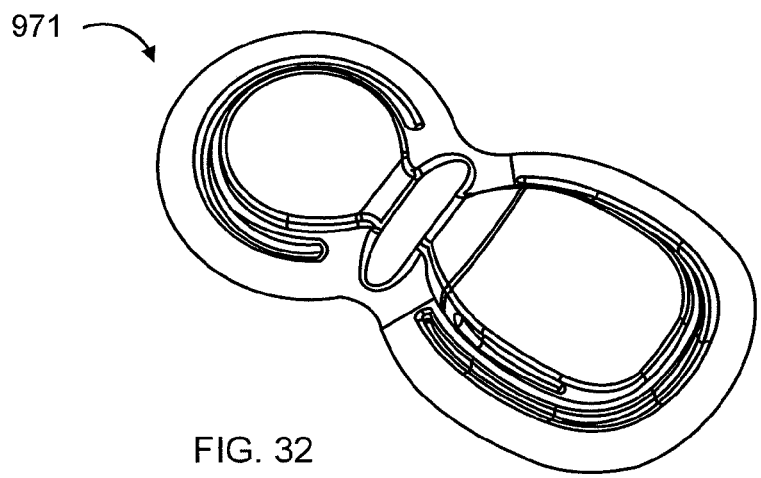
Figure 33:
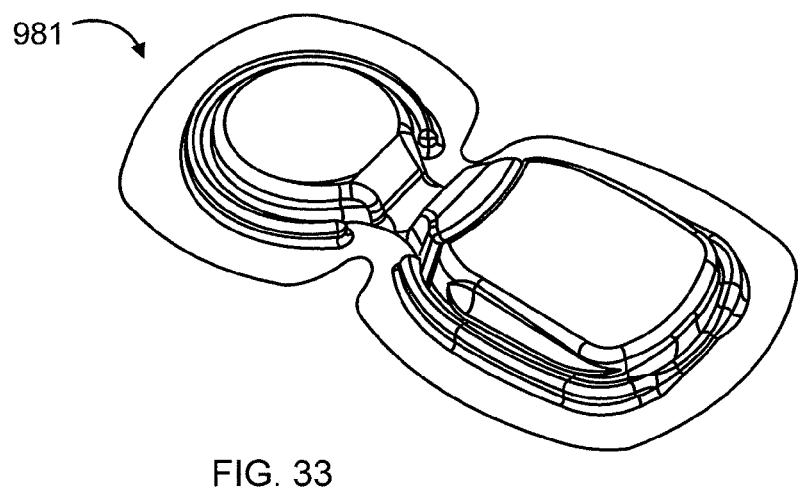

Although the apparatus have been illustrated and described herein as having a certain outer shape and/or profile, in other embodiments, an apparatus can have a different outer shape and/or profile. For example, an apparatus can have an outer shape and/or profile like that of apparatus 961, 971, and/or 981, as illustrated in FIGS. 31-33.

Thus, the breadth and scope of the invention should not be limited by any of the above-described embodiments, but should be defined only in accordance with the following claims and their equivalents. The previous description of the embodiments is provided to enable any person skilled in the art to make or use the invention. While the invention has been particularly shown and described with reference to embodiments thereof, it will be understood by those skilled in the art that various changes in form and details may be made therein without departing from the spirit and scope of the invention.

Figure 34:
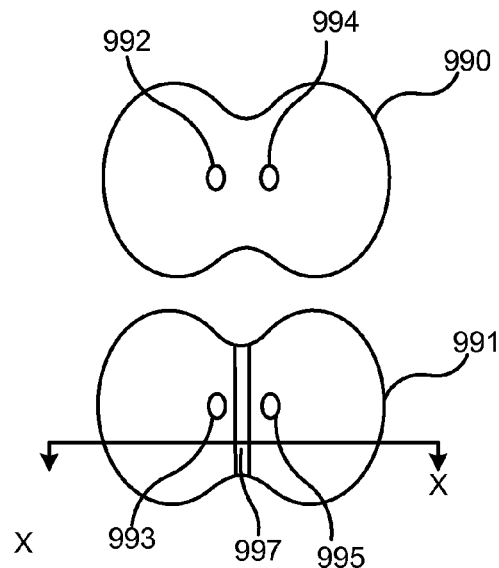
FIG. 34 is a top view of two experimental apparatus according to embodiments.
Figure 35:
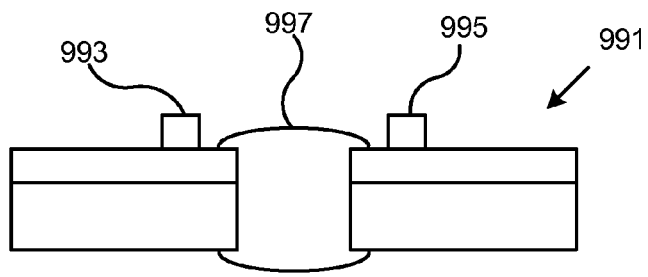
FIG. 35 is a cross-sectional view of an apparatus of FIG. 20 taken along line X-X.

An experiment was performed utilizing a first apparatus 990 and a second apparatus 991 according to an embodiment of the invention, as illustrated in FIG. 34, to estimate the leakage current when each of the first apparatus and the second apparatus is immersed in solutions encountered during daily activities. Apparatus 990 includes a first metal connector 992 and a second metal connector 994. Apparatus 991 was cut in the middle and the cut was filled with hot glue 997 to increase impedance between a first metal connector 993 and a second metal connector 995, as illustrated in FIGS. 34 and 35. Impedance of both direct current (DC) and alternating current (AC) was measured between the two metal connectors 992, 994 of the first apparatus 990. Impedance of both DC and AC was measured between the two metal connectors 993, 995 of the second apparatus 991 prior to submersion in the liquid. AC impedance was measured between the two metal connectors 992, 994 of the first apparatus 990 while the first apparatus was attached to skin of a patient. AC impedance was measured between the two metal connectors 993, 995 of the second apparatus 991 while the second apparatus was attached to the skin of the patient.

Figure 36:
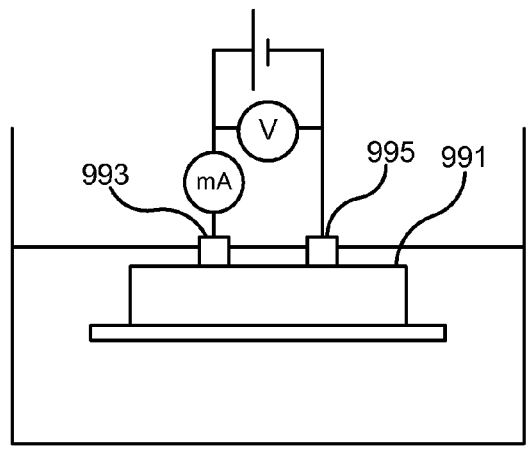
FIG. 36 is a front view of an apparatus of FIG. 20 partially immersed in a liquid.

Each of the first apparatus 990 and the second apparatus 991 was submerged in a liquid with a 3V Lithium coin battery attached to its respective metal connectors, as illustrated in FIG. 36 with reference to apparatus 991. The discharge current and voltage were each measured for each apparatus 990, 991 when the apparatus was submerged. Each of the discharge current, voltage and impedance were measured after removing the each apparatus 990, 991 from its respective liquid submersion. Additionally, each of the discharge current, voltage and impedance were measured after slight wiping of the each apparatus 990, 991. Each apparatus 990, 991 was then washed with tap water. These steps were performed for each of the following liquids: tap water, hot tub water, and saline solution. The discharge current showed an expected battery discharge, while AC impedance may represent leakage of the stimulation current on the patch rather than through bodily tissue. All AC impedance measurements were performed at 1 KHz. The results are shown in Table 1, below.

TABLE 1

Effects of Various Liquids on the Apparatus*

| | Apparatus 990 | | Apparatus 991 | |
| --- | --- | --- | --- | --- |
| | Battery current | Impedance | Battery leakage | Impedance |
| Submersion in tap water | 1.5 mA | | 1.6 mA | |

TABLE 1-continued

Effects of Various Liquids on the Apparatus*

| | Apparatus 990 | | Apparatus 991 | |
|---|---|---|---|---|
| | Battery current | Impedance | Battery leakage | Impredance |
| Removal from tap water | 0.6 mA | 2.0 Kohm 27 nF | 0.1 mA | ∞ Kohm 49 pF |
| After wiping | 0.3 mA | 300 Kohm 2.0 nF | >0.1 mA | ∞ Kohm 30 pF |
| Submersion in hot tub water | 2 mA | | 2.2 mA | |
| Removal from hot tub water | 0.8 mA | 2.0 Kohm 13 nF | 0.07 mA | 1.7 Kohm 1.2 nF |
| After wiping | 0.5 mA | 90 Kohm 1.0 nF (130 Kohm after absorbing water with napkin) | >0.01 mA | 230 Kohm 128 pF |
| Submersion in saline solution | 9 mA | | 10 mA | |
| Removal from saline solution | 0.4 mA | 0.34 Kohm 212 nF | 0.04 mA | 3.5 Kohm 1.7 nF |
| After wiping | 0.3 mA | 0.5 Kohm 134 nF | >0.01 mA | 230 Kohm 94 nF |

*Before submersion, DC impedance approached infinity; AC impedance R approached infinity, C = pF; Impedance on the skin (AC) R = 8.3 Kohm, C = 36 nF. Battery voltage (when connected to the immersed patch) was 2.8-2.9 v.

The results indicate that daily use of a bath or hot tub for 20 minutes drains 0.5-0.7 mAh per use (or 3.5-4.9 mAh per week). Assuming that the apparatus 991 incorporates a power source similar to a cr2032 coin lithium battery (225 mAh capacity), this drain is insignificant. A daily swim in ocean water for 20 minutes will drain ~3.3 mAh per day (or ~21 mAh per week), which is insignificant when compared to the suggested power source capacity. Further, the current drain during the drying period of 1 hour (for apparatus 990) is less than 1 mA per use (7 mAh per week) and does not add significant discharge compared with the power source capacity. After removal from the liquid, apparatus 991, which has a hydrophobic plastic barrier (similar to barrier 218 described above) ensures significantly lower power source discharge current compared to apparatus 990, which lacks a barrier. A significant amount of electrical current escapes via apparatus 990 and would not be expected to reach the body when apparatus 990 is exposed to liquid. However, apparatus 991 would be expected to divert most of the electrical current to the body, if wiped.

What is claimed is:

1. An apparatus, comprising:
   a substrate having a first surface and a second surface different than the first surface, a first portion of the first surface of the substrate being non-parallel to a second portion of the first surface of the substrate;
   an electrode assembly including a first electrode and a second electrode different than the first electrode, the electrode assembly being coupled to the second surface of the substrate and being configured to facilitate transmission of an electrical current from an external stimulator through a bodily tissue;
   a coupling mechanism configured to removably couple the external stimulator to the substrate, the coupling mechanism defining a receiving portion configured to receive therein at least a portion of the external stimulator, the coupling mechanism including a protrusion configured to matingly engage the external stimulator when the portion of the external stimulator is received within the receiving portion of the coupling mechanism such that a position of the external stimulator is rigidly fixed with respect to the electrode assembly;
   a power source being coupled to the substrate and being configured to provide power to the external stimulator; and
   a connection assembly including a first mechanical connector and a second mechanical connector coupled to the first surface of the substrate, each of the first mechanical connector and the second mechanical connector being disposed on the first portion of the first surface of the substrate, the connection assembly having a first configuration in which the first mechanical connector and the second mechanical connector are electrically coupled to the external stimulator and a second configuration in which the first mechanical connector and the second mechanical connector are electrically isolated from the external stimulator, when the connection assembly is in its first configuration, the connection assembly is configured to complete a power circuit between the power source and the external stimulator and a stimulation circuit between the external stimulator and the electrode assembly.

2. The apparatus of claim 1, wherein the substrate includes a first layer and a second layer, at least one of the power source, the first mechanical connector, the second mechanical connector, and electrical circuitry being at least partially embedded in the first layer, the second layer of the substrate being formed over a portion of the electrode assembly.

3. The apparatus of claim 1, wherein the substrate includes a first layer and a second layer, the first layer being formed of a first material, the second layer being formed of a second material different than the first material, the second material being non-conductive.

4. The apparatus of claim 1, wherein the substrate is flexible.

5. The apparatus of claim 1, wherein the power source has a positive terminal and a negative terminal, the first mechanical connector of the connection assembly is configured to electrically couple the external stimulator to the positive terminal of the power source and to the first electrode.

6. The apparatus of claim 1, wherein the power source has a positive terminal and a negative terminal, the second mechanical connector of the connection assembly is configured to electrically couple the external stimulator to the negative terminal of the power source and to the second electrode.

7. The apparatus of claim 1, further comprising a diode configured to allow the electrical current to flow in a first direction between the first electrode and the second electrode, the diode configured to substantially inhibit flow of the electrical current between the first electrode and the second electrode in a second direction opposite the first direction.

8. The apparatus of claim 1, further comprising a capacitor configured to separate an alternating current from a direct current, the capacitor configured to substantially inhibit flow of the direct current from the power source to the first electrode.

9. The apparatus of claim 1, further comprising a capacitor configured to separate an alternating current from a direct current, the capacitor configured to deliver at least one of the alternating current and the direct current from the external stimulator to the first electrode.

10. The apparatus of claim 1, wherein a connector of the connection assembly is configured for wireless electrical communication between the battery and the external stimulator.

11. The apparatus of claim 1, wherein a connector of the connection assembly is configured for wireless electrical communication between an electrode of the electrode assembly and the external stimulator.

12. The apparatus of claim 1, wherein a connector of the connection assembly is a coil configured to wirelessly transmit an electrical output to the external stimulator.

13. The apparatus of claim 1, further comprising:
an oscillator coupled to the substrate, the oscillator configured to deliver an oscillation to a coil coupled to the substrate to initiate wireless transmission of an electrical output from the coil to the external stimulator.

14. The apparatus of claim 1, wherein a connector of the connection assembly is an antenna configured to wirelessly communicate an electrical current between the external stimulator and at least one of the power source and the electrode assembly.

15. The apparatus of claim 1, further comprising:
electrical circuitry disposed on the first surface of the substrate; and
wherein the substrate includes a tab portion, at least a portion of the electrical circuitry is disposed on the first surface of the substrate on the tab portion, the tab portion configured to be folded such that the tab portion of the substrate is in contact with the second surface of the substrate and such that the electrical circuitry disposed on the first surface of the substrate extends about an outer edge of the fold.

16. The apparatus of claim 1, further comprising:
a housing disposable over a portion of the substrate, a surface of the housing defining a recess configured to removably receive at least a portion of the external stimulator.

17. The apparatus of claim 1, wherein the protrusion of the coupling mechanism is configured to matingly engage a first end of the external stimulator different than a second end of the external stimulator configured to engage at least one of the first mechanical connector and the second mechanical connector, when the external stimulator is received in the receiving portion of the coupling mechanism.

18. The apparatus of claim 1, wherein the connection assembly includes only the first mechanical connector and the second mechanical connector for electrically coupling the external stimulator to each of the power source and the electrode assembly.

19. An apparatus, comprising:
a substrate having a first surface and a second surface different than the first surface, a first portion of the first surface of the substrate being non-parallel to a second portion of the first surface of the substrate;
an electrode assembly including a first electrode and a second electrode different than the first electrode, the electrode assembly being coupled to the second surface of the substrate and being configured to facilitate transmission of an electrical current from an external stimulator through a bodily tissue;
a power source being coupled to the substrate and being configured to provide power to the external stimulator; and
a connection assembly including a first mechanical connector and a second mechanical connector coupled to the first surface of the substrate, each of the first mechanical connector and the second mechanical connector being disposed on the first portion of the first surface of the substrate,
the connection assembly having a first configuration in which the first mechanical connector and the second mechanical connector are electrically coupled to the external stimulator and a second configuration in which the first mechanical connector and the second mechanical connector are electrically isolated from the external stimulator, when the connection assembly is in its first configuration, the connection assembly is configured to complete a power circuit between the power source and the external stimulator and a stimulation circuit between the external stimulator and the electrode assembly,
the first portion of the first surface of the substrate upon which the first mechanical connector and the second mechanical connector are disposed being external to the external stimulator when the connection assembly is in its first configuration.

\* \* \* \* \*